United States Patent [19]

Mallams

[11] 4,063,015

[45] Dec. 13, 1977

[54] GARAMINE AND DERIVATIVES THEREOF

[75] Inventor: Alan K. Mallams, West Orange, N.J.

[73] Assignee: Schering Corporation, Kenilworth, N.J.

[21] Appl. No.: 596,799

[22] Filed: July 17, 1975

Related U.S. Application Data

[63] Continuation of Ser. No. 391,914, Aug. 27, 1973, abandoned, which is a continuation-in-part of Ser. No. 296,434, Oct. 10, 1972, abandoned, which is a continuation-in-part of Ser. No. 327,263, Jan. 29, 1973, abandoned, and a continuation-in-part of Ser. No. 308,061, Nov. 20, 1972, abandoned.

[51] Int. Cl.$^2$ ............................................. C07H 15/22
[52] U.S. Cl. .................................... 536/17; 195/31 P; 424/180; 424/181; 536/4; 536/18
[58] Field of Search ........ 260/210 AB, 210 K, 210 R; 536/4, 17

[56] References Cited

U.S. PATENT DOCUMENTS

| 3,268,508 | 8/1966 | Sugazawa et al. | 260/210 AB |
|---|---|---|---|
| 3,651,042 | 3/1972 | Marquez et al. | 260/210 AB |
| 3,915,955 | 10/1975 | Cooper et al. | 260/210 AB |

*Primary Examiner*—Johnnie R. Brown
*Attorney, Agent, or Firm*—Raymond A. McDonald; Stephen B. Coan; Bruce M. Eisen

[57] ABSTRACT

This disclosure relates to the preparation of garamine, its use as an antibacterial, and its use as an intermediate in the novel processes for preparing novel pseudotrisaccharides containing a garamine moiety, and to the use of the novel pseudotrisaccharides as antimicrobial, anthelmintic, antiprotozoal and antiviral agents.

18 Claims, No Drawings

GARAMINE AND DERIVATIVES THEREOF

This application is a continuation application of application Ser. No. 391,914, filed Aug. 27, 1973 now abandoned, which in turn is a continuation-in-part of application Ser. No. 296,434, filed Oct. 10, 1972 (now abandoned), and Ser. No. 327,263, filed Jan. 29, 1973 (now abandoned), being a continuation-in-part of application Ser. No. 308,061, filed Nov. 20, 1972 (now abandoned).

In one aspect of this invention, this application relates to novel pseudotrisaccharides, their pharmaceutically acceptable acid addition salts and Schiff's base oxazolidine derivatives, and to the use of such compounds as antimicrobial, antiprotozoal, anthelmintic and antiviral agents.

In another aspect this application relates to garamine, garamine derivatives and to the processes for their obtention and conversion to pseudotrisaccharides. In still another aspect, this application relates to the preparation of certain monosaccharides and derivatives thereof and to use of such compounds in the preparation of pseudotrisaccharides.

More particularly, in its composition aspect, this invention relates to novel pseudotrisaccharides of the formula:

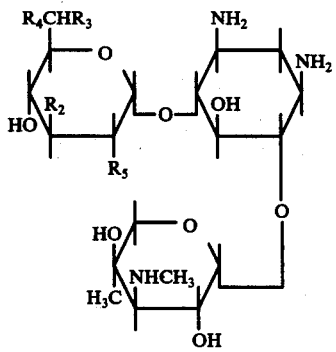

I and their pharmaceutically acceptable acid addition salts and Schiff's base oxazolidine derivatives, wherein $R_2$ is hydrogen or hydroxy, $R_3$ and $R_5$ are each hydroxy or $NHR_4$, $R_4$ is hydrogen or lower alkyl with the provisos (a) that when $R_2$ is hydroxy, $R_4$ is H or $CH_3$ and $R_3$ is OH or $NH_2$, then $R_5$ is other than $NH_2$; (b) that when both $R_2$ and $R_5$ are hydroxy, and $R_4$ is H or $CH_3$ then $R_3$ is other than $NH_2$. The term "lower alkyl" embraces those alkyl radicals having from 1 to 4 carbon atoms, particularly methyl. The compounds of formula I (including those known compounds excluded by the proviso provisions) have valuable anthelmintic, antiprotozoal, antimicrobial and antiviral activity.

In its process aspects, this invention relates to the preparation of pseudotrisaccharides of the formula:

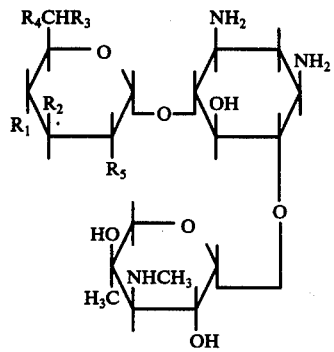

Ia wherein $R_1$ is hydrogen or hydroxy, $R_2$ is hydrogen or hydroxy, each of $R_3$ and $R_5$ are hydroxy or $NHR_4$, and $R_4$ is hydrogen or lower alkyl.

As can be seen upon visual inspection of structural formula I, garamine, 0-3-deoxy-4-C-methyl-3-(methylamino)-β-L-arabinopyranosyl-(1→6)-2-deoxy-D-streptamine is the pseudodisaccharide common to the pseudotrisaccharides of this invention. This compound is represented by the formula:

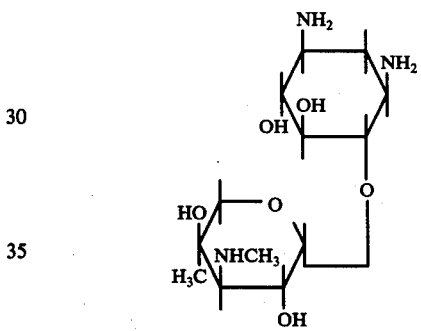

II

In general the preparation of the pseudotrisaccharides of formulae I and Ia is effected by certain condensation procedures wherein "blocked" or "protected" garamine is caused to react with an appropriately prepared D-glucopyranosyl monosaccharide to produce the "blocked" or "protected" garamine derivatives which are designed to render the molecule selectively non-reactive, thus enabling the condensation (also referred to as glycosylation) to take place at the desired reactive site. Suitable selectively blocked garamine intermediates useful for producing the pseudotrisaccharides of formulae I and Ia are represented by the structural formula:

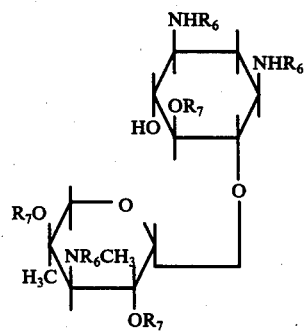

II wherein each $R_6$ is an amino protective group and each $R_7$ is a hydroxy protective group. It should be noted, however, that although it is preferred to utilize those garamine intermediates which are fully protected, it is also possible to use those intermediates wherein either some or all of the hydroxy groups are protected. Thus although $R_7$ is preferably defined as a hydroxy protective group, it can also represent hydrogen. For convenience, in those instances wherein any one or all of the amino or hydroxy functions are protected the intermediate will be referred to as a selectively-blocked garamine. The term "amino protective group" is well known in organic chemistry and refers to a large number of groups suitable for temporarily blocking (synonymous with protecting) an amino moiety in a molecule from undergoing chemical reactions, yet are readily removable after a desired chemical reaction is effected in other sites in the molecule. Exemplifying these groups are unsubstituted, as well as functionally substituted aryl, arylalkyl, acyl, alkoxycarbonyl, and arylalkoxycarbonyl groups. These groups are defined in accordance with their standard art meaning as set forth in standard chemical references, see *Advances in Organic Chemistry, Methods and Results,* Raphael, R. A., Taylor, E. C., and Wynberg, H., Vol. 3, Interscience Publishers, New York, 1963, pp. 159–162, 191–193. Common examples of amino protective groups are benzyl, 4-nitrobenzyl, triphenylmethyl and 2,4-dinitrophenyl groups. Exemplifying specific acyl groups are acetyl, propionyl and benzoyl groups. Specific examples of alkoxycarbonyl groups are methoxycarbonyl, ethoxycarbonyl, 2,2,2-trichloroethoxycarbonyl, t-butoxycarbonyl, and 2-iodoethoxycarbonyl groups. Exemplifying the arylalkoxycarbonyl groups are carbobenzoxy, and 4-methoxybenzyloxycarbonyl groups. Particularly preferred is the carbobenzoxy group.

The term "hydroxy protective groups," used synonymously with alcoholic hydroxy protective groups, similarly is a well known term in the art and refers to those groups suitable for temporarily blocking and thereby protecting a hydroxy moiety in a molecule from undergoing chemical reactions, yet are readily removable after a desired chemical reaction is effected in other sites in the molecule. These groups are defined in accordance with their standard art meaning set forth in standard chemical references, see, *Advances in Organic Chemistry*, supra, pp. 216–228, 269–276. Exemplifying these groups are acyl, benzyl, and carbobenzoxy groups. "Acyl," as used herein is meant in its broad terminology as an organic radical derived from an organic acid by the removal of the hydroxyl group, e.g. R.CO is the radical of R.CO.OH.

The selectively-blocked garamine may be derived from a pseudotrisaccharide having a garamine moiety and a hex-4-enopyranoside moiety. Exemplifying a particularly suitable pseudotrisaccharide from which the selectively-blocked garamine may be produced is sisomicin, also known as Antibiotic 66-40, which has been shown to be 0-2,6-diamino-2,3,4,6-tetradeoxy-α-D-glycerohex-4-enopyranosyl-(1→4)-O-[3-deoxy-4-C-methyl-3-(methylamino)-β-L-arabinopyranosyl-(1→6)]-2-deoxy-D-streptamine, and may be represented by the structural formula:

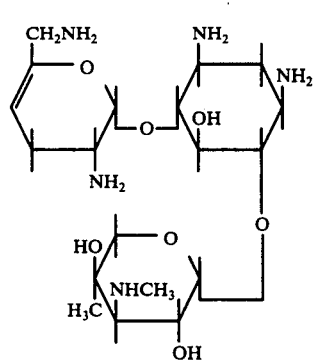

III and may be produced by the microbiological fermentation of *Micromonospora inyoensis* (NRRL 3292) according to the procedures described in Belgian Pat. No. 735,145. Sisomicin is particularly suitable for producing a selectively-blocked garamine as the fermentation process leading to the production of sisomicin produces no substantial amounts of co-produced antibiotics.

Garamine, as the free base, may be produced by deblocking the selectively-blocked garamine derivatives according to standard procedures, e.g. catalytic hydrogenation, and/or alkaline hydrolysis, preferably alkaline hydrolysis.

When desired, garamine, can be converted into acid addition salts in a conventional manner. The acids preferred for this conversion are those which yield physiologically acceptable salts. Thus, organic and inorganic acids are used, such as, for example, aliphatic, alicyclic, araliphatic, aromatic, or heterocyclic mono- or polybasic carboxylic or sulfonic acids, such as formic acid, acetic acid, propionic acid, diethylacetic acid, oxalic acid, malonic acid, succinic acid, pimelic acid, fumaric acid, maleic acid, lactic acid, tartaric acid, malic acid, amino-carboxylic acids, benzoic acid, salicyclic acid, phenylpropionic acid, citric acid, gluconic acid, ascorbic acid, cinnamic acid, or hydrohalic acids, such as hydrochloric acid. These acid addition salts generally are more readily soluble than the corresponding base. Garamine may also be converted into the corresponding Schiffs-base oxazolidine according to standard techniques for effecting such a conversion.

When garamine is derived directly from microbiological fermentation, synthetically, or by cleaving a moiety containing garamine, the selectively-blocked garamine may be prepared according to the teachings of this invention and affords the same routes to the preparation of gentamicin $X_2$ and other pseudotrisaccharides consisting of a garamine moiety and a monosaccharide moiety. Garamine, as will hereinafter be discussed, is useful in its own right as an antibacterial agent.

For purposes of clarity, when describing the preparation of a selectively-blocked garamine, or garamine as the free base, sisomicin will be used as the starting material to exemplify the procedure although other pseudotrisaccharides having the garamine and hex-4-enopyranoside moieties are equally suitable.

Generally, sisomicin is first selectively-blocked according to standard techniques for blocking amino groups with an appropriate amino protective group. The molecule (IV) is then cleaved by acid hydrolysis, or oxidative routes to yield a selectively-blocked garamine and a sugar in the case of the hydrolytic route and selectively-blocked garamine in the oxidative route.

In those instances wherein garamine is desired, the blocked garamine having the amino groups protected, may be deblocked as described before by such methods as catalytic hydrogentation, or preferably alkaline hydrolysis. When it is desired to obtain the gentamicin $X_2$ without going to the garamine, the molecule is then preferably selectively-blocked with an appropriate hydroxy protective group.

The selectively-blocked garamine in which only the amino groups are protected may be also used directly to obtain the pseudotrisaccharides embraced herein, although it is preferable to also selectively-block the hydroxy functions. The hydrolysis of the pseudotrisaccharide (IV) is unexpected and the ease with with it proceeds is contrary to the teachings in the art. (See *The Amino Sugars*, Vol. 1A, Jeanloz and Balazs, Academic Press, 1969.)

The above-described reaction may be depicted by the following reaction scheme:

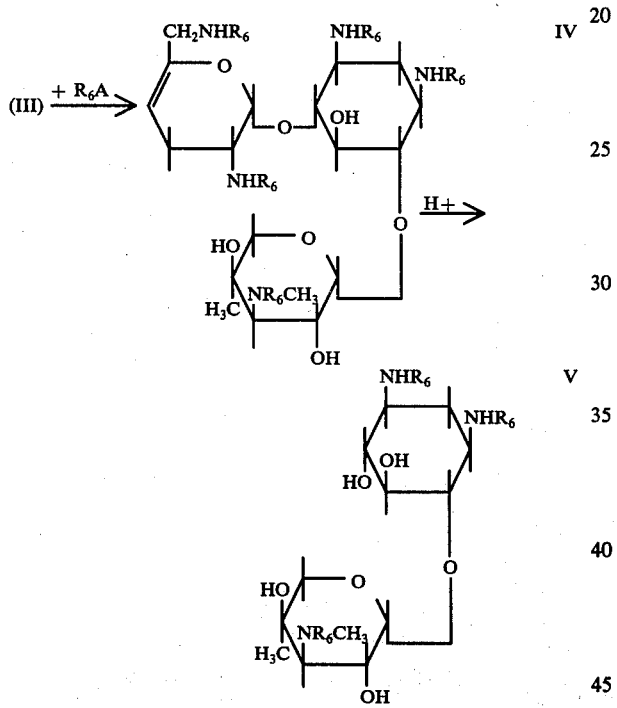

wherein $R_6$ is an amino protective group, and A is a suitable carrier for said amino protective group.

When hydrolytic means are employed to cleave the selectively-blocked pseudotrisaccharide (IV) the reaction is conducted in a suitable inert solvent such as tetrahydrofuran, dioxane, methanol, or chloroform. The pH of the solution is adjusted to about one using any standard acidic reagent such as para-toluenesulphonic acid, sulphuric acid, hydrochloric acid, or acid ion exchange resin, e.g. Amberlite IR 120, (H+), giving the desired selectively-blocked garamine (V). When the oxidative route is employed to accomplish the cleavage either hypobromous acid in the presence of barium carbonate, or organic peracids, e.g. metachloroperbenzoic acid, may be employed.

The selectively-blocked garamine (V) may then be further protected by blocking the 4-hydroxy group only with a suitable protecting group $R_8$, followed by further protection of the remaining hydroxy groups with a different protecting group R to give the selectively-blocked garamine derivatives (VI) and (VII) respectively. The requirements for the hydroxy protective groups $R_8$ and $R_7$ are such that $R_8$ must be stable under the reaction conditions used to introduce $R_7$, and $R_7$ must be stable under the reaction conditions used to convert the selectively-blocked garamine (VII) to the desired selectively-blocked garamine (VIII).

The foregoing reaction scheme may be depicted as follows:

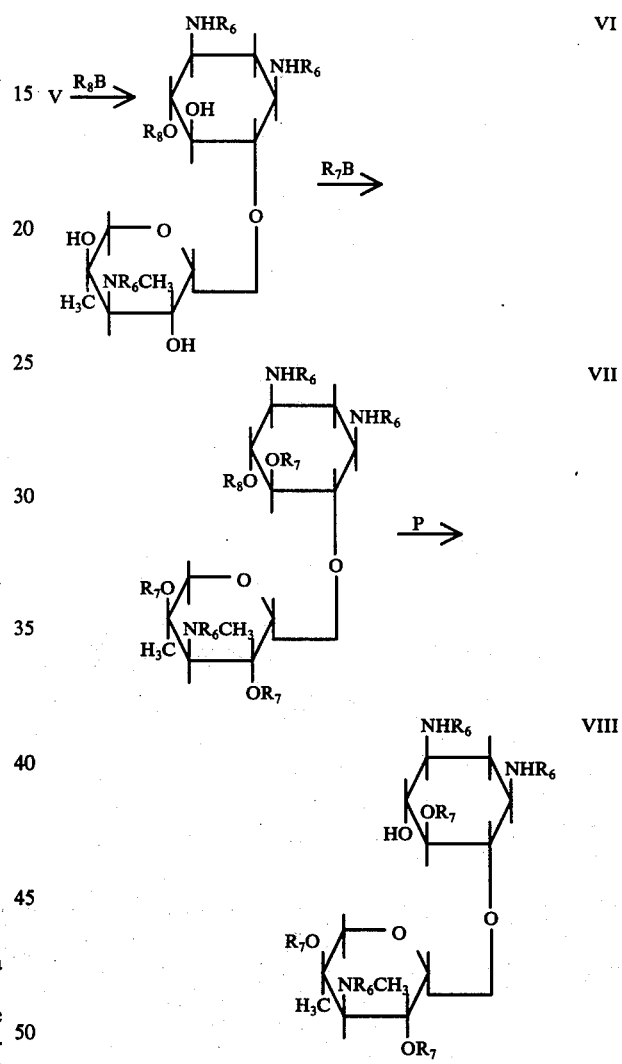

wherein $R_6$ is as previously defined, $R_8$ and $R_7$ are each hydroxy protective groups, with the proviso that $R_8$ is stable under conditions used to introduce $R_7$ and $R_7$ is stable under conditions used to remove $R_8$, P is a standard reagent used to effect selective removal of the hydroxy-protective group $R_8$, and B is a suitable carrier for said hydroxy protective groups.

The selectively-blocked garamine (VI) may also be further protected under suitable conditions to give the derivative (IX) which may be converted to the desired selectively-blocked garamine (X) under appropriate reaction conditions.

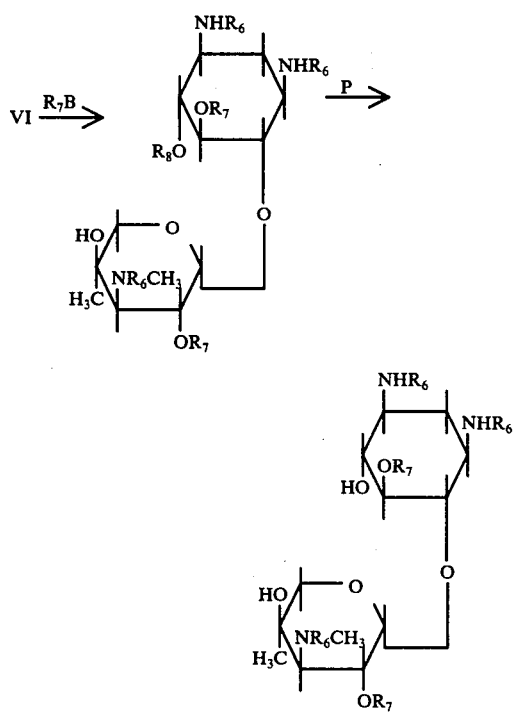

wherein $R_6$, $R_8$, $R_7$, B and P are as previously defined.

Alternatively the selectively-blocked garamine (V) after initial protection of the vicinal glycol system to give (XI), may be further protected to give (XII) which on selective removal of the glycol protective group gives the desired selectively-blocked garamine (XIII).

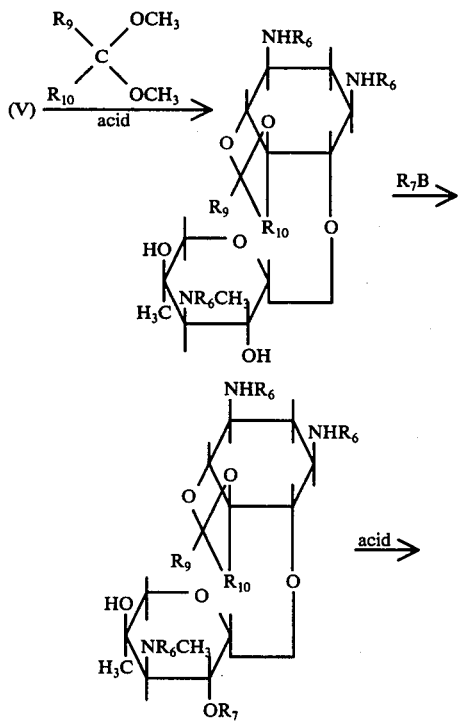

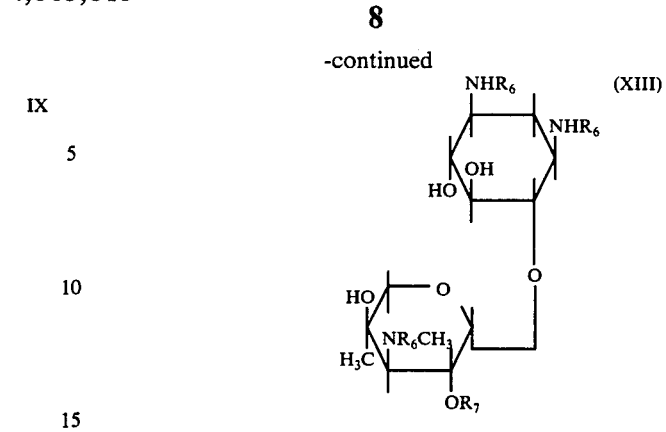

wherein $R_6$, $R_7$, B and P are as previously defined and $R_9$ and $R_{10}$ are each lower alkyl, or $R_9$ is aryl and $R_{10}$ is hydrogen.

The selectively-blocked garamine derivatives (V), (VIII), (X) and (XIII) may then be transformed into the pseudotrisaccharides of formula Ia by standard glycosylation procedures known to those skilled in the art, of which the Koenigs-Knorr and Lemieux reactions are examples.

The foregoing reaction may be exemplified by the following reaction scheme which depicts the Koenigs-Knorr reaction:

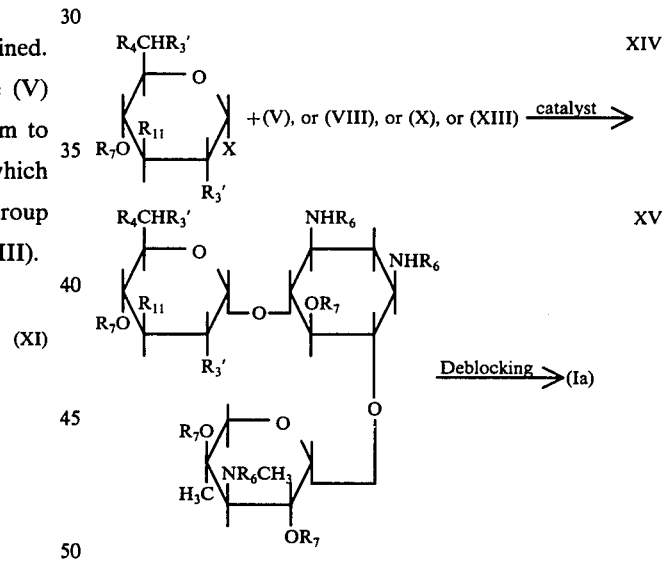

wherein $R_{11}$ is H or a hydroxy protecting group, $R_4$, $R_6$ and $R_7$ are as previously defined and X is a halogen atom, e.g. a chloro, or bromo atom, and $R_3'$ is a protected OH or protected amino group. The above reaction is usually carried out in the presence of a suitable catalyst, e.g. mercuric cyanide, mercuric bromide, silver carbonate, silver oxide, silver perchlorate, or silver tosylate. Suitable inert organic solvents for conducting the foregoing reactions include dioxane, tetrahydrofuran, acetonitrile, nitromethane, toluene and benzene.

The resultant selectively-blocked pseudotrisaccharides (XV) are then deblocked according to standard procedures for removing hydroxy and amino protective groups.

The Lemieux reaction may be depicted by the following reaction scheme:

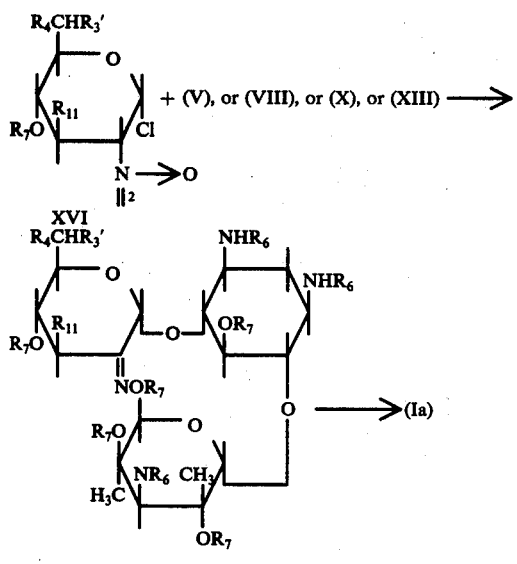

wherein $R_3$, $R_4$, $R_7$, $R_6$, are as previously defined.

The above reaction is usually carried out in a suitable inert organic solvent, e.g. dimethylformamide, or methylene chloride. The protected pseudotrisaccharide oxime (XVII) is then reduced, e.g. with diborane in a suitable inert organic solvent and is subsequently de-blocked according to standard procedures to give the pseudotrisaccharide of formula Ia.

Another reaction scheme suitable for the preparation of compounds of this invention is shown in the following series of formulae.

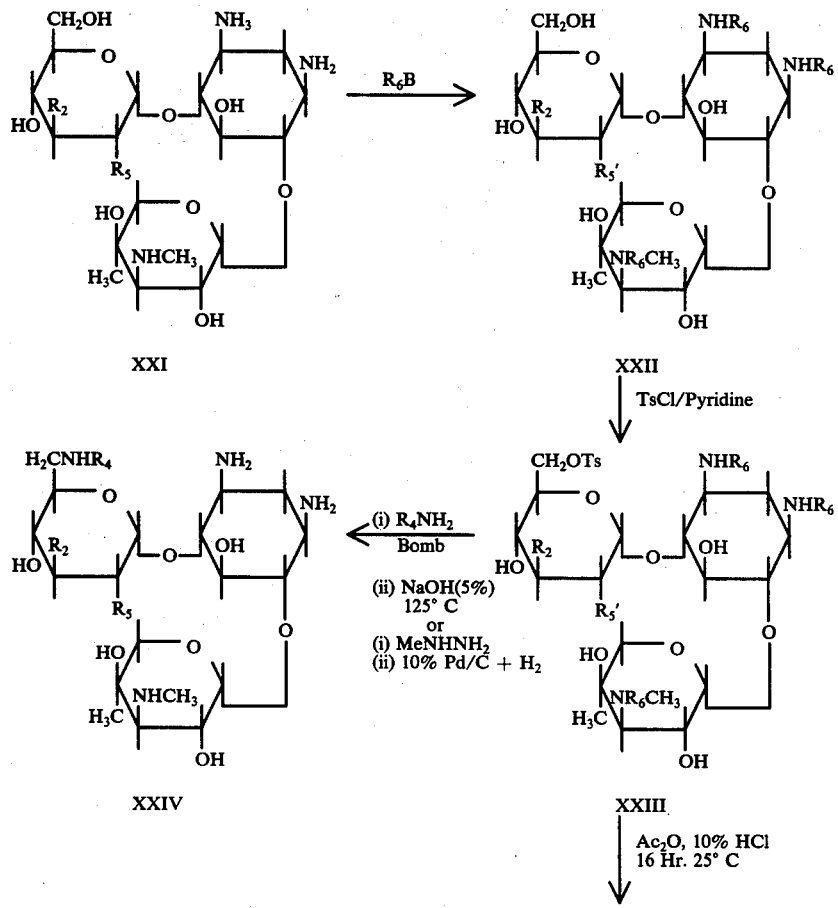

-continued
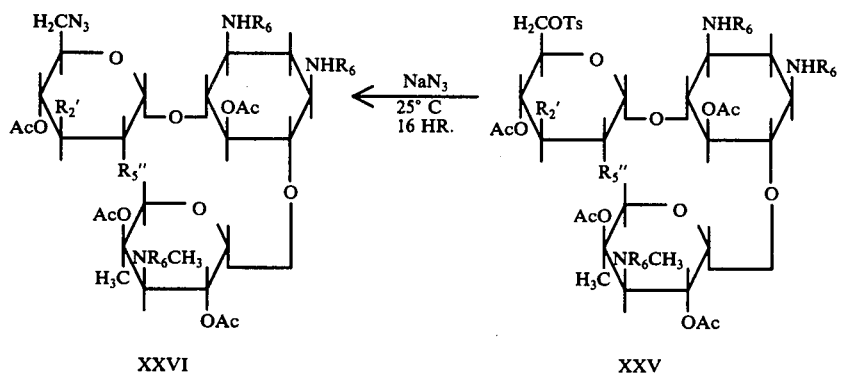
XXVI  XXV
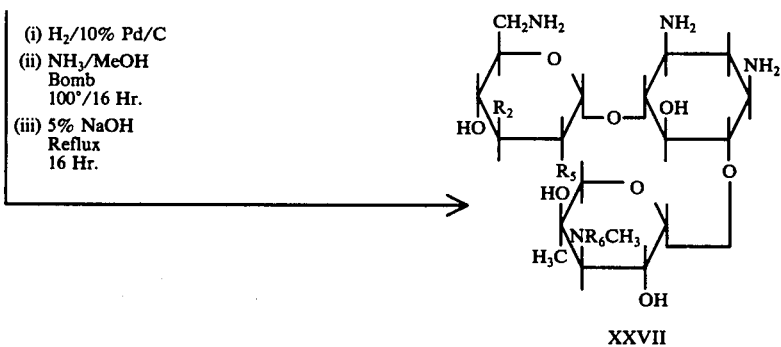
(i) H₂/10% Pd/C
(ii) NH₃/MeOH Bomb 100°/16 Hr.
(iii) 5% NaOH Reflux 16 Hr.
XXVII
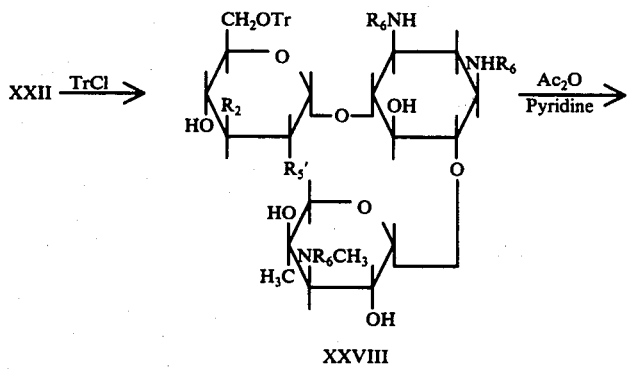
XXVIII
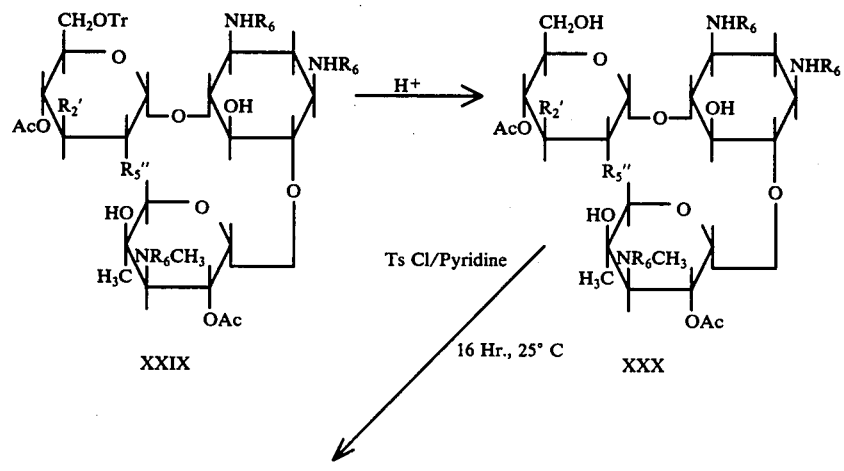
XXIX  XXX

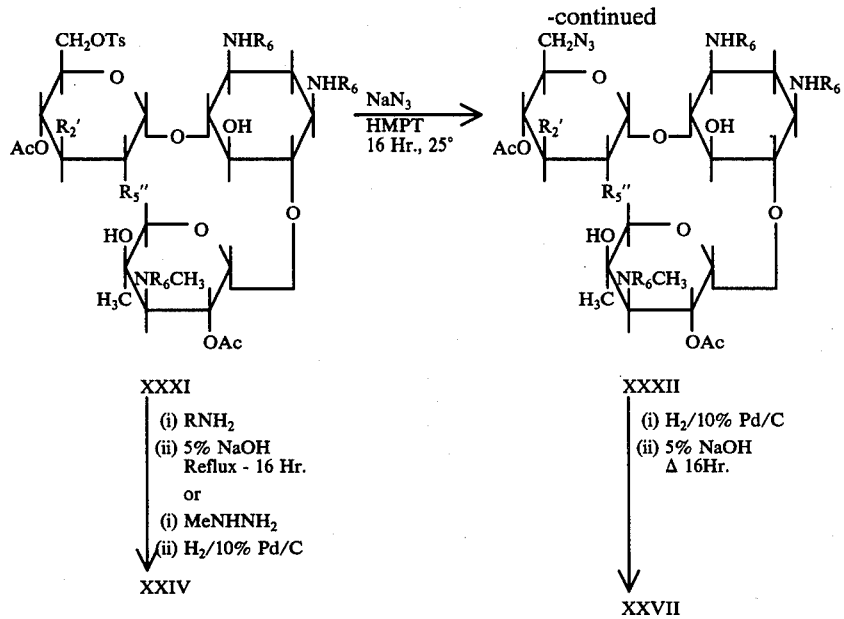

XXXI (i) RNH₂
(ii) 5% NaOH
   Reflux - 16 Hr.

or (i) MeNHNH₂
(ii) H₂/10% Pd/C

XXIV

XXXII (i) H₂/10% Pd/C
(ii) 5% NaOH
   Δ 16Hr.

XXVII

The foregoing reaction schemes (XXI→XXXII) is a schematic representation showing the preparation of 6 α-amino and 6'-alkylamino pseudotrisaccharides from the corresponding 6'-OH compounds. In the reactions $R_5$ is OH or $NHR_4$; $R_5'$ is $NR_4R_6$ or OH; $R_5''$ is $NR_4R_6$ or OAc, and $R_2'$ is OAc or H. Exemplary of this reaction is 3'-deoxy-6'-N-methyl-JI-20A prepared from 3 +-deoxygentamicin by conversion of 3'-deoxygentamicin $X_2$ by the N-carbobenzoxy derivative followed by tritylation of the primary hydroxy group, acetylation of the 4'- and 2''-hydroxy groups, detritylation and tosylation to give the desired 6'-tosyl trisaccharide. Treatment of the latter with excess methylamine in methanol in a bomb followed by deblocking with base gave 3'-deoxy-6'-N-methyl-JI-20A.

The following examples are illustrative of methods for preparing selectively-blocked garamine derivatives, garamine and pseudotrisaccharides from said selectively-blocked garamine derivatives.

In the following examples the symbol † is used to indicate a mixture of rotamers at ambient temperatures.

EXAMPLE 1

1,3,2',6',3''-Penta-N-carbobenzoxysisomicin

Sisomicin (25 g.), and sodium carbonate (13 g.) were dissolved in distilled water (625 ml.). Carbobenzoxy chloride (100 ml.) was added to the stirred solution at 25°, and the mixture was stirred for 16 hours. The solid was filtered off, washed thoroughly with water, dried in vacuo, and then washed with hexane to give 1,3,2',6',3''-penta-N-carbobenzoxysisomicin (62 g.) (99%) as a colorless amorphous solid. Chromatography on silica gel plates using 40% acetone in benzene as the eluent gave an analytical sample, m.p. 165°-173° (dec.), (Found: C, 63,53; H, 6.23; N, 6.28. $C_{59}H_{67}N_5O_{17}$ requires: C, 63.41; H, 5.99; N, 6.27%), $[\alpha]_D^{26}$ + 96.2° ($CH_3OH$), ν max ($CHCl_3$) 3400, 1720, 1515, 1215, 1050, 695 cm.⁻¹, δ ($CDCl_3$) † 1.03 (3H, broad singlet, 4''-$CH_3$), 3.02 (3H, broad singlet, 3''—N—$CH_3$), 5.02 (10H, broad singlet, —$CH_2C_6H_5$), and 3.28, 3.30 ppm. (25H, broad singlets, —$CH_2C_6H_5$).

EXAMPLE 2

1,3,3'-Tri-N-carbobenzoxygaramine i. 1,3,2',6',3''-Penta-N-carbobenzoxysisomicin (436 g.) was dissolved in tetrahydrofuran (3 liters), and Amberlite I.R. 120 (H+) resin (1 kg.) was added. The mixture was allowed to stand at 25° for 3 days and was then filtered, and the resin was washed with tetrahydrofuran. The combined filtrates were evaporated in vacuo in the presence of a few ml. of water to give the crude product as a gum. Chromatography on silica gel using 10% methanol in chloroform as the eluent gave 1,3,3'-tri-N-carbobenzoxygaramine (200 g.) (71%) as a colorless amorphous solid, m.p. 104°-112°, (Found: C, 60.12; H, 5.83; N, 5.63. $C_{37}H_{45}N_3O_{12}$ .$H_2O$ requires: C, 59.92; H, 6.34; N, 5.67%), $[\alpha]_D^{26}$ + 69.6° ($C_2H_5OH$), λ max ($CH_3OH$) 206 mμ (ε28,000) and 258 mμ (ε538), ν max ($ChCl_3$) 3350, 1700, 1525, 694 cm.⁻¹, δ ($CDCl_3$) † 0.99 (3H, broad s, 4'—$CH_3$), 3.00 (3H, broad s, 3'—$NCH_3$), 5.00 (6H, broad s, —$CH_2C_6H_5$), 7.20 ppm. (15H, multiplet, —$CH_2C_6H_5$), δ (DMSO at 120°) 0.96 (3H, s, 4'—$CH_3$), 2.99 (3H, s, 3'—$NCH_3$), 5.02, 5.05, 5.11 (2H each, s, —$CH_2C_6H_5$), and 3.31 ppm. (15H, s, —$CH_2C_6H_5$).

ii. 1,3,2',6',3''-Penta-N-carbobenzoxysisomicin (100 mg.) was dissolved in tetrahydrofuran (20 ml.) acidified to pH 1 with concentrated sulphuric acid, and the solution was allowed to remain at 25° for 16 hours. The reaction mixture was passed through Amberlite IR45 resin, and the eluent was evaporated, and the residue was chromatographed on silica gel plates using 10% methanol in chlorofrom as the eluent to give 1,3,3'-tri-N-carbobenzoxygaramine (40 mg.) (62%) as a colorless amorphous solid having identical physical characteristics to those described in (i) above.

iii. 1,3,2',6',3''-Penta-N-carbobenzoxysisomicin (1.25 g.) was chromatographed on silica gel using 10% methanol in chloroform as the eluent to give 1,3,3'-tri-N-carbobenzoxygaramine (450 mg.) (56%) as a colorless amorphous solid having identical physical characteristics to those described in (i) above.

iv. 1,3,2',6',3''-Penta-N-carbobenzoxysisomicin (3 g.), sodium bicarbonate (0.9 g.), and m-chloroperbenzoic acid (0.9 g.) were dissolved in tetrahydrofuran (75 ml.) containing water (3.75 ml.), and the mixture was stirred at 25° for 16 hours. The reaction mixture was evaporated, and the residue was partitioned between water and chloroform. The chloroform solution was dried (MgSO$_4$), evaporated to dryness, and the residue was chromatographed on a silica gel column using 7% methanol in chloroform as the eluent to give 1,3,3'-tri-N-carbobenzoxygaramine (0.52 g.) (27%) as a colorless amorphous solid the physical characteristics identical to those described in (i) above.

v. 1,3,2',6',3''-Penta-N-carbobenzoxygaramine (3 g.), and barium carbonate (0.6 g.) in tetrahydrofuran (100 ml.), were treated with hypobromous acid (26 ml.) (prepared from 3.6 g. bromine in 100 ml. of water), and the mixture was stirred at 25° for 16 hours. The reaction mixture was concentrated, and the residue was partitioned between water and chloroform. The chloroform solution was dried (MgSO$_4$), evaporated, and the residue was chromatographed on silica gel using 7% methanol in chloroform as the eluent to give 1,3,3'-tri-N-carbobenzoxygaramine (84 mg.) (4%) as a colorless amorphous solid the physical characteristics identical to those described in (i) above.

EXAMPLE 3

1,3,3'-Tri-N-carbothoxygaramine

Sisomicin (2 g.) was dissolved in water containing sodium bicarbonate (4 g.). Ethyl chloroformate (5 ml.) was added and the mixture was stirred at 25° for 16 hours. The reaction mixture was extracted with chloroform and the latter was washed with water, dried (MgSO$_4$) and evaporated. The resulting gum was taken up in tetrahydrofuran (100 ml.) and treated with Amberlite IR120 resin (30 g.) and the mixture was stirred at 25° for 72 hours. The product was eluted off the resin with methanol and the eluate was evaporated and chromatographed on a silica gel column (110 × 2.5 cm.) using 10% methanol in chloroform as the eluent, to give 1,3,3'-tri-N-carbethoxygaramine (1.0 g.) as a colorless amorphous solid, m.p. 128°-140°, (Found: C, 48.63; H, 7.25; N, 7.64. C$_{22}$H$_{39}$N$_3$O$_{12}$ requires: C, 49.18; H, 7.26; N, 7.82%), m/e 537 (M+), [α]$_D^{26}$ +99.2° (CH$_3$OH), ν max (CHCl$_3$) 3330, 1700, 1530, 1050, 1040 cm.$^{-1}$, δ (CDCl$_3$) † 1.20 (12H, broad m, 4'—CH$_3$ and —NH-COOCH$_2$CH$_3$), 3.01 (3H, broad s, 3'—NCH$_3$), 6.10 ppm. (6H, broad m, —NHCOOCH$_2$CH$_3$).

EXAMPLE 4

Garamine i. 1,3,3'-Tri-N-carbobenzoxygaramine (2.02 g.) was dissolved in methanol (100 ml.), and 10% palladium on carbon (1.0 g.) was added. The mixture was hydrogenated at 25° at 50 lbs/sq. in. for 16 hours, and the catalyst was filtered off, and washed with methanol. The filtrate was evaporated, and chromatographed on silica gel using the lower phase of a chloroform-methanol-concentrated ammonium hydroxide (2:1:1) system as the eluent. The fractions containing the garamine were concentrated in vacuo to small volume, and were then passed through Amberlite IR45 resin. The eluate was concentrated to small volume in vacuo, and the resulting solution was lyophilized to give garamine (750 mg.) (84%) as a colorless amorphous solid, m.p. 89°-99°, (Found: C, 48.31; H, 8.54; N, 12.87. C$_{13}$H$_{27}$N$_3$O$_6$ requires: C, 48.60; H, 8.41; N, 13.08%), m/e 322 (M+ +1), [α]$_D^{26}$ + 135.4° (H$_2$O), pKa 8.5, ν max (nujol) 3300, 1060 cm.$^{-1}$, δ (D$_2$O) 1.19 (3H, s, 4'—CH$_3$), 2.51 (3H, s, 3'—NCH$_3$), 2.57 (1H, d, J$_{2',3'}$=10.5 Hz, H$_{3'}$), 3.30 )1H, d, J$_{5'a,5'e}$=12.5 Hz, H$_{5'a}$), 3.79 (1H, dd, J$_{2',3'}$=10.5 Hz, J$_{1',2'}$=4 Hz, H$_{2'}$), 4.03 (1H, d, J$_{5'a,5'e}$=12.5 Hz, H$_{5'e}$), 5.06 ppm. (1H, d, J$_{1',2'}$=4 Hz, H$_{1'}$).

ii. 1,3,3'-Tri-N-carbobenzoxygaramine (500 mg.) and sodium hydroxide (2 g.) were dissolved in dioxane-water (1:1) (40 ml.) and the solution was heated under reflux for eighteen hours. The solution was cooled and neutralized with Amberlite IRC-50 ion exchange resin. The resin was washed with water and then eluted with 1.5 M ammonium hydroxide solution. The alkaline eluent was collected, evaporated to dryness and chromatographed as in (i) above to garamine (215 mg.) (97%) which was identical with that prepared in (i) above.

EXAMPLE 5

1,3,3'-Tri-N-carbobenzoxy-4-0-(2,2,2-trichloroethylcarbonyl)-garamine 1,3,3'-Tri-N-carbobenzoxygaramine (1 g.) was dissolved in dry pyridine (18 ml.), and the mixture was cooled to 0°. 2,2,2-Trichloroethylchloroformate (dried over molecular sieves) (323 mg.) was added dropwise with stirring. The funnel was rinsed with dry pyridine (4 ml.) which was added to the reaction mixture. Stirring was continued for 30 minutes until the initially formed precipitate had dissolved, and the reaction mixture was then stored at 7° for 45 hours. The solution was poured into water, and the precipitate was extracted with ethyl acetate. The ethyl acetate extracts were washed with water, 2N hydrochloric acid, water, dried (MgSO$_4$), filtered, and evaporated in vacuo. The residue was azeotroped with toluene, concentrated to small volume, and triturated with chloroform. The insoluble 1,3,3'-tri-N-carbobenzoxy-4-0-(2,2,2,-trichloroethylcarbonyl)-garamine (1.1 g.) (87%) was obtained as colorless needles, m.p. 220-222°, (Found: C, 53.49; H, 5.36; N, 4.77. C$_{40}$H$_{46}$N$_3$O$_{14}$Cl$_3$ requires: C, 53.43; H, 5.16; N, 4.67%), [α]$_D^{26}$+ 65.9° (CH$_3$OH), λmax (CH$_3$OH) 207 mμ (ε 26,200), νmax (nujol) 3450, 3280, 1770, 1700, 1680, 1050, 697 cm.$^{-1}$, δ (CDCl$_3$) † 1.26 (3H, broad s, 4'-CH$_3$), 3.05 (3H, broad s, 3'—NCH$_3$), 4.73 (2H, s, Cl$_3$CCH$_2$OCOO—), and 7.33 ppm. (15H, broad s, —CH$_2$$\overline{C_6H_5}$).

EXAMPLE 6

5,2',4'-Tri-O-acetyl-1,3,3'-tri-N-carbobenzoxy-4-0-(2,2,2,-trichloroethylcarbonyl)-garamine i. 1,3,3'-Tri-N-carbobenzoxy-4-0(2,2,2,-trichloroethylcarbonyl)-garamine (16.5 g.) was dissolved in glacial acetic acid (500 ml.) and freshly redistilled trifluoroacetic anhydride (133 ml.) and p-toluenesulphonic acid (750 mg.) were added to the stirred solution. The reaction mixture was stirred at 25° for 20 hours, and was then poured into ice-water, and the precipitate that formed was extracted into ethyl acetate. The latter extract was washed with water, 5% sodium bicarbonate, water dried (MgSO$_4$), filtered, and evaporated to give 5,2',4'-tri-0-acetyl-1,3,3'-tri-N-carbobenzoxy-4-0-(2,2,2-trichloroethylcarbonyl)-garamine (18.8 g.) (99%) as a colorless amorphous solid, m.p. 92-100°, (Found: C, 54.23; H, 5.48; N, 4.25; Cl, 9.55. C$_{46}$H$_{52}$N$_3$O$_{17}$Cl$_3$ requires: C, 54.15; H, 5.11; N, 4.10; Cl, 10.37%), [α]$_D^{26}$ + 69.0 ° (CHCL$_3$), λmax (CH$_3$OH) 203 mμ (ε 24,950), νmax (CHCL$_3$) 1770, 1740, 1220, 1055, 695 cm.$^{31}$ $^1$, δ (CDCl$_3$) † 1.35 (3H, broad s, 4'-CH$_3$), 1.93, 2.04 (9H, broad s, OAc), 2.90 (3H, broad s, 3'—NCH$_3$), 4.70 (2H, broad s, OCH₂CCl₃), and 7.33 ppm. (15H, broad s, —CH₂C₆H₅), ii. 1,3,3'-Tri-N-carbobenzoxy-4-0-(2,2,2-trichloroethylcarbonyl)-garamine (1 g.) was dissolved in glacial acetic acid (50 ml.), and a mixture of acetic anhydride (4.5 ml.), and concentrated hydrochloric acid (0.5 ml.) was added. The solution was heated on a steam bath for three hours, and the reaction was worked up as in (i) above to give 5,2'-tri-O-acetyl-1,3,3'-tri-N-carbobenzoxy-4-0(2,2,2-trichloroethylcarbonyl)-garamine (1.12 g.) (99%) as a colorless solid which was identical with that prepared in (i) above.

iii. 1,3,3,'-Tri-N-carbobenzoxy-4-0-(2,2,2-trichloroethylcarbonyl)-garamine (1 g.) and a mixture of acetic anhydride (9 ml.) and concentrated hydrochloric acid (1 ml.) were stirred at 25°. The initially insoluble material gradually went into solution and the solution was stirred for eighteen hours. The mixture was poured into water, extracted with ethyl acetate and the latter was washed with 5% aqueous sodium bicarbonate, water, and was then dried (MgSO₄), filtered and evaporated to give 5,2',4'-tri-O-acetyl-1,3,3'-tri-N-carbobenzoxy-4-0-(2,2,2-trichloroethylcarbonyl)-garamine (1.1 g.) (98%) as a colorless solid which was identical with that prepared in (i) above.

EXAMPLE 7
5,2',4'-Tri-0-acetyl-1,3,3'-tri-N-carbobenzoxygaramine 5,2',4'-Tri-O-acetyl-1,3,3'-tri-N-carbobenzoxy-4-0-(2,2,2-trichloroethylcarbonyl)-garamine (16.6 g.) was dissolved in 90% acetic acid (650 ml.) and powdered zinc (100 g.) was added to the stirred solution. Stirring was continued at 25° until no starting material remained as demonstrated by t.l.c. The zinc was filtered off and the aqueous acid was removed in vacuo affording a residue which was taken up in ethyl acetate, washed with water, dried (MgSO₄), filtered, and evaporated to give 5,2',4'-tri-O-acetyl-1,3,3'-tri-N-carbobenzoxygaramine which was chromatographed on a silica gel columen (100 × 5 cm.) using 1% methanol in chloroform as the eluent to give a colorless amorphous solid (12.2 g.) (89% ) m.p. 101°–105°, (Found: C, 60.86; H, 6.42; N, 4.98. $C_{43}H_{51}N_3O_{15}$ requires: C, 60.77; H, 6.05; N, 4.94%), $[\alpha]_D^{16}$ + 83.1° (CH₃OH), λmax (CH₃OH) 207 mμ (ε 26,500), ν max (CHCl₃) 3480, 1740, 1710, 1220, 1035, 694 cm.$^{311}$, δ (CDCl₃) † 1.30, 1.40 (3H, broad s, 4'-CH₃), 1.95, 2.05, 2.08, (9H, broad s, OAc), 2.88 (3H, broad s, 3'—NCH₃), and 7.34 ppm. (15H, broad s, —CH₂C₆H₅).

EXAMPLE 8
5,2'-Di-O-acetyl-1,3,3'-tri-N-carbobenzoxy-4-0-(2,2,2-trichloroethylcarbonyl)-garamine i. 1,3,3'-Tri-N-carbobenzoxy-4-0-(2,2,2,-trichloroethylcarbonyl)-garamine (4.2 g.) was dissolved in dry pyridine (100 ml.) and treated with acetic anhydride (42 ml) and the mixture was allowed to remain at 25° for 6 days. The solution was poured into water, and extracted with chloroform. The chloroform extract was dried (MgSO₄), filtered and evaporated and the residue was chromatographed on a silica gel column (160 × 2.5 cm.) using 2% methanol in chloroform as the eluent to give 5,2'-di-O-acetyl-1,3,3'-tri-N-carbobenzoxy-4-0-(2,2,2-trichloroethylcarbonyl)-garamine (4.3 g.) (96%) as a colorless amorphous solid, m.p. 115°–120°, (Found: C, 53.79; H, 5.14; N, 3.91; Cl, 10.73. $C_{44}H_{50}N_3O_{16}Cl_3$ requires: C, 53.76; H, 5.13; N, 4.27; Cl, 10.82%) $[\alpha]_D^{26}$ + 64.2° (CH₃OH), νmax (CHCl₃) 3390, 1760, 1720, 1230, 1050 cm.$^{-1}$, δ(CDCl₃) † 1.00, 1.10 (3H, broad s, 4'—CH₃), 1.87, 2.03 (6H, broad s, OAc), 2.89 (3H, broad s, 3'—NCH₃), 5.02 (6H, broad s, —CH₂C₆H₅), and 7.25 ppm. (15H, broad m, —CH₂C₆H₅).

ii. 1,3,3'-Tri-N-carbobenzoxy-4-0-(2,2,2-trichloroethylcarbonyl)-garamine (500 mg.) was dissolved in dry pyridine (25 ml.) and treated with acetic anhydride (5 ml.) and the mixture was heated under reflux on a steam bath for 16 hours. The solution was evaporated to small volume, poured into water, and extracted with chloroform. The chloroform extract was dried (MgSO₄), filtered and evaporated and the residue was chromatographed on a silica gel column (110 × 2.5 cm.) using 1% methanol in chloroform as the eluent to give 5,2'-di-O-acetyl-1,3,3'-tri-N-carbobenzoxy-4-O-(2,2,2-trichloroethylcarbonyl)-garamine (480 mg.) (90%) which was identical with that prepared in (i) above.

EXAMPLE 9
5,2'-Di-O-acetyl-1,3,3'-tri-N-carbobenzoxygaramine 5,2'-Di-O-acetyl-1,3,3'-tri-N-carbobenzoxy-4-O-(2,2,2-trichloroethylcarbonyl)-garamine (1 g.) was dissolved in 90% acetic acid (100 ml.), and powdered zinc (7 g.) was added to the stirred solution. Stirring was continued at 25° until no starting material remained (2 hours). The zinc was filtered off and the aqueous acetic acid was removed in vacuo affording a residue which was taken up in ethyl acetate, washed with water, dried (MgSO₄), filtered and evaporated. The residue was chromatographed on a silica gel column (160 × 2.5 cm.) using 4% methanol in chloroform as the eluent to give 5,2'-di-O-acetyl-1,3,3'-tri-N-carbobenzoxygaramine (0.8 g.) (98%) as a colorless amorphous solid, m.p. 115°–122°, (Found: C, 60.21; H, 6.07; N, 5.22. $C_{41}H_{49}N_3O_{14}$ requires: C, 60.97; H, 6.07; N, 5.20%), $[\alpha]_D^{26}$ + 62.8° (CH₃OH), νmax (CHCl₃) 3350, 1720, 1220, 1040 cm.$^{-1}$, δ(CDCl₃) † 0.98, 1.07 (3H, broad s, 4'—CH₃), 1.85, 2.08 (6H, broad s, OAc), 2.87 (3H, broad s, 3'—NCH₃), 5.00 (6H, broad s, —CH₂C₆H₅), and 7.27 ppm. (15H, broad m, —CH₂C₆H₅).

EXAMPLE 10
1,3,3'-Tri-N-carbobenzoxy-4,5-O-isopropylidenegaramine 1,3,3'-Tri-N-carbobenzoxygaramine (5 g.), 2,2-dimethoxypropane (6.2 ml.), and p-toluenesulphonic acid (0.06 g.) were dissolved in dry dimethylformamide (30 ml.), and the solution was heated under reflux at 110° for four hours. The reaction mixture was cooled, and passed through a Dowex 1 × 2 (OH—) resin, and the methanol eluate was concentrated, and diluted with water to give the product. The latter was chromatographed on silica gel using 2% methanol in chloroform as the eluent to give 1,3,3'-tri-N-carbobenzoxy-4,5-O-isopropylidenegaramine (3.72 g.) (70%) as a colorless amorphous solid, m.p. 126°–129°, (Found: C, 61.12; H, 6.33; N, 5.01. $C_{40}H_{49}N_3O_{12}\cdot H_2O$ requires: C, 61.46; H, 6.53; N, 5.38%), $[\alpha]_D^{26}$ + 87.3° (C₂H₅OH), πmax (CH₃OH) 208 mμ (ε24,800), νmax (CHCl₃) 3400, 3280, 1690, 1540, 1055, 694 cm.$^{-1}$ δ(CDCl₃) † 1.03 (3H, broad s, 4'—CH₃), 1.40 (6H, broad s,

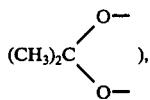

3.02 (3H, broad s, 3'—NCH₃), 4.82, 5.09 (6H, broad singlets, —CH₂C₆H₅), 7.08, and 7.30 ppm. (15 H, multiplets, —CH₂C₆H₅), δ(DMSO at 140°) 0.98 (3H, s, 4'—CH₃),1.40 (6H, s,

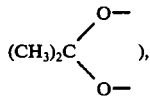

3.02 (3H, s, 3'—NCH₃), 5.08 (4H, s, —CH₂C₆H₅), 5.12 (2H, s, —CH₂C₆H₅), and 7.33 ppm. (15H, s, —CH₂C₆H₅).

EXAMPLE 11

2'-O-Acetyl-1,3,3'-tri-N-carbobenzoxy-4,5-O-isopropylidenegaramine 1,3,3'-Tri-N-carbobenzoxy-4,5-O-isopropylidenegaramine (1.6 g.) in dry pyridine (10 ml.) was treated with acetic anhydride (2 ml.), and the mixture was heated at 100° for 20 hours. The reaction mixture was poured into ice water, and the solid that separated was filtered off, and chromatographed on silica gel using 7% methanol in chloroform as the eluent to give 2'-O-acetyl-1,3,3'-tri-N-carbobenzoxy-4,5-O-isopropylidenegaramine (1.22 g.) (72%) as a colorless amorphous solid, m.p. 105°–108°, (Found: C, 62.55; H, 6.52; N, 5.35. C₄₂H₅₁N₃O₁₃ requires: C, 62.63; H, 6.33; N, 5.22%), [α]$_D^{26}$ + 77.5° (C₂H₅OH), λmax (CH₃OH) 208 mμ (ε25,300), νmax (CHCl₃) 3400, 3300, 1730, 1700, 1520, 1220, 1050, 697 cm.⁻¹, δ(CDCl₃) † 1.08 (3H, broad s, 4'-CH₃), 1.39 (6H, broad s,

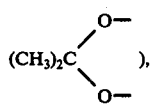

1.91 (3H, broad s, 2'-OAc), 2.91 (3H, broad s, 3'-NCH₃), 4.97–5.17 (6H, broad singlets, —CH₂C₆H₅),7.23, and 7.31 ppm. (15H, broad singlets, —CH₂C₆H₅), δ(DMSO at 140°) 1.01 (3H, s, 4'—CH₃), 1.37 (6H, s,

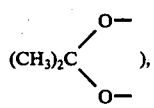

1.90 (3H, s, 2'—OAc), 2.90 (3H, s, 3'-NCH₃), 5.03, 5.06, 5.13 (6H, singlets, —CH₂C₆H₅), 5.33 (1H, d, J₁',₂'=3Hz, H₁'), and 7.32 ppm. (15H, s, —CH₂C₆H₅).

EXAMPLE 12

2'-O-Acetyl-1,3,3'-tri-N-carbobenzoxygaramine

2'-O-acetyl-1,3,3'-tri-N-carbobenzoxy-4,5-O-isopropylidenegaramine (150 mg.) was dissolved in 80% aqueous acetic acid (5 ml.), and the solution was allowed to stand at 25° for 16 hours. The mixture was evaporated to dryness, and the residue was chromatographed on silica gel plates using 10% methanol in chloroform as the eluent to give 2'-O-acetyl-1,3,3'-tri-N-carbobenzoxygaramine (118 mg.) (83%) as a colorless amorphous solid, m.p. 103°–107°, (Found: C, 60.81; H, 6.28; N, 5.54. C₃₉H₄₇N₃O₁₃ requires: C, 61.20; H, 6.14; N, 5.49%), [α]$_D^{26}$ + 66.6° (C₂H₅OH), λmax (CH₃OH) 208 mμ (ε24,800), νmax (CHCl₃) 3410, 1730, 1700, 1515, 1220, 1040, 696 cm.⁻¹, δ(CDCl₃) † 1.04 (3H, broad s, 4'—CH₃), 1.88 (3H, broad s, 2'—OAc), 2.89 (3H, broad s, 3'—NCH₃), 4.98, 5.08 (6H, broad singlets, —CH₂C₆H₅), and 7.23 ppm. (15H, broad s, —CH₂C₆H₅), δ(DMSO at 140°), 1.04 (3H, s, 4'—CH₃), 1.90 (3H, s, 2'—OAc), 2.90 (3H, s, 3'—NCH₃), 5.02, 5.06, 5.14 (6H, singlets, —CH₂C₆H₅), 5.33 (1H, d, J₁',₂'=3Hz, H₁'), and 7.33 ppm. (15H, s, —CH₂C₆H₅).

EXAMPLE 13

1,3,2',6',3''-Penta-N-acetylsisomicin

Sisomicin (500 mg.) was dissolved in methanol (25 ml.), and acetone (25 ml.), and acetic anhydride (8 ml.) was added. Additional methanol (50 ml.) was added after a half hour, and the mixture was allowed to stand at 25° for 3 hours. Concentration in vacuo followed by chromatography on silica gel using the lower phase of a chloroform-methanol-concentrated ammonium hydroxide (1:1:1) system as the eluent gave 1,3,2',6',3''-penta-N-acetylsisomicin (660 mg.) (90%) as a colorless amorphous solid, m.p. 188°–198° (dec.), (Found: C, 52.45; H, 7.26; N, 10.44. C₂₉H₄₇N₅O₁₂ requires: C, 52.95; H, 7.20; N, 10.65%), m/e 639 (M⁺-18), [α]$_D^{26}$ + 194.6° (CH₃OH), νmax (nujol) 3300, 1650, 1550, 1025 cm.⁻¹, δ(CD₃OD) † 1.01, 1.10 (3H, s, 4''-CH₃), 1.90, 1.96, 1.99, 2.15 (15H, s, NAc), 3.01, 3.13 (3H, s, 3''—NCH₃), 5.19 (1H, d, J₁'',₂''=4Hz, H₁''), and 5.54 ppm. (1H, d, J₁',₂'=2.5Hz, H₁'), δ(DMSO at 140°) 0.97 (3H, s, 4''-CH₃), 1.76 (3H, s, NAc), 1.79 (3H, s, NAc), 1.82 (3H, s, NAc), 1.86 (3H, s, NAc), 1.99 (3H, s, NAc), 2.97 (3H, s, 3''—NCH₃), 5.09 (1H, multiplet, H₁''), and 5.32 ppm. (1H, d, J₁',₂'=2.5Hz, H₁').

EXAMPLE 14

1,3,3'-Tri-N-acetylgaramine i. Garamine (500 mg.) in methanol (17 ml.) was treated with acetic anhydride (2.5 ml.), and the mixture was allowed to remain at 25° for 20 minutes. Evaporation to dryness, and chromatography of the residue on silica gel plates using the lowere phase of a chloroform-methanol-concentrated ammonium hydroxide (1:1:1) system as the eluent gave 1,3,3'-tri-N-acetylgaramine (450 mg.) (65%) as a colorless amorphous solid, m.p. 190°–195°, (Found: C, 49.80; H, 7.59; N, 9.34. C₁₉H₃₃N₃O₉ . H₂O requires: C, 49.03; H, 7.53; N, 9.03%), m/e 447 (M⁺), [α]$_D^{26}$ + 101.4° (C₂H₅OH), νmax (nujol) 3240, 1650, 1550, 1050 cm.⁻¹, (CD₃OD) † 1.02,1.12 (3H, s, 4'-CH₃), 1.93, 1.98, 2.18 (9H, s, NAc), 3.05, 3.17 (3H, s, 3'-NCH₃), and 5.22 ppm. (1H, d, J₁',₂'=4Hz, H₁'), δ(DMSO at 170°) † 1.00, 1.28 (3H, s, 4'—CH₃), 1.81, 1.83, 2.03 (9H, s, NAc), 2.81, 3.01 (3H, s, 3'—NCH₃), and 5.13 ppm. (1H, multiplet, H₁').

ii. Sisomicin (1 g.), and thiolacetic acid (2 ml.) were dissolved in a mixture of methanol (4 ml.), and acetone (2 ml.), and the mixture was photolysed in a sealed quartz tube at 35° for 90 hours using 3000A low pressure mercury lamps. The solution was passed down an Amberlite I.R. 45 column, and eluted with methanol. Evaporation of the eluate followed by chromatography on silica gel using the lower phase of a chloroform-methanol-concentrated ammonium hydroxide (1:1:1)

system as the eluent, gave 1,3,3'-tri-N-acetylgaramine (0.47 g.) (47%) as a colorless solid with identical physical characteristics to those described in (i) above, and 1,3,2',6',3''-penta-N-acetylsisomicin (0.46 g.) (31%) as a colorless amorphous solid.

EXAMPLE 15

1,3,2',6',3''-Penta-N-acetyl-5,2''-di-O-acetylsisomicin

Sisomicin (6 g.) and 4-dimethylaminopyridine (66 mg.) were dissolved in pyridine (120 ml.), and acetic anhydride (28 ml.) was added. The mixture was stirred at 25° for 17 hours. Methanol was added and the mixture was allowed to stand for a further 4 hours, and was then evaporated, and the residue was azeotroped with toluene until free of pyridine. Chromatography on silica gel using 10% methanol in chloroform as the eluent gave 1,3,2',6',3''-penta-N-acetyl-5,2''-di-O-acetylsisomicin (9 g.) (91%) as a colorless amorphous solid, m.p. 160°–175°, (Found: C, 51.85; H, 6.50; N, 9.43. $C_{33}H_{51}N_5O_{14} \cdot H_2O$ requires: C, 52.16; H, 7.03; N, 9.22%), m/e 741 (M+), $[\alpha]_D^{26}$ + 174.5° ($CH_3OH$), $\nu$max (nujol) 3280, 1750, 1650, 1550, 1230, 1050 cm.$^{-1}$, $\delta(CD_3OD)$ † 1.02, 1.10 (3H, s, 4''—$CH_3$), 1.88–2.24 (21H, singlets, NAc and OAc), 2.88, 3.00 (3H, s, 3'—$NCH_3$), 5.20 (1H, broad multiplet, $H_{1''}$), and 5.40 ppm. (1H, broad multiplet, $H_{1'}$).

EXAMPLE 16

1,3,3'-Tri-N-acetyl-5-O-acetylgaramine i. 1,3,2',6',3''-Penta-N-acetyl-5,2''-di-O-acetylsisomicin (10 g.) was dissolved in dioxan (300 ml.) containing water (15 ml.). Sodium bicarbonate (3.66 g.), and m-chloroperbenzoic acid (3.66 g.) were added, and the mixture was stirred at 25° for 22 and a half hours. The reaction mixture was diluted with methanol (150 ml.), and passed through a 10 × 2 cm. bed of basic alumina. The eluate was concentrated to dryness, and the residue was chromatographed on silica gel using 10% methanol in chloroform as the eluent to give 1,3,3'-tri-N-acetyl-5-O-acetylgaramine (2.24 g.) (31%) as a colorless amorphous solid, m.p. sublimes at 139°, and melts at 188°–195°, (Found: C, 50.17; H, 7.26; N, 8.17. $C_{23}H_{37}N_3O_{11} \cdot H_2O$ requires: C, 50.26; H, 7.15; N, 7.65%), m/e 531 (M+), $[\alpha]_D^{26}$ + 102.5° ($CH_3OH$), $\nu$max (nujol) 3300, 1740, 1650, 1550, 1235, 1050 cm.$^{-1}$, $\delta$ ($CD_3OD$) † 1.01, 1.14 (3H, s, 4'—$CH_3$), 1.87–2.12 (15H, singlets, NAc, and OAc), 2.91, and 3.00 ppm. (b 3H, s, 3'—$NCH_3$), $\delta$(DMSO at 130°) 1.00 (3H, s, 4'-$CH_3$), 1.74, 1.81, 1.92, 2.00 (12H, s, NAc and OAc), and 2.87 ppm. (3H, s, 3'—$NCH_3$).

ii. 1,3,2',6',3''-Penta-N-acetyl-5,2''-di-O-acetylsisomicin (2 g.) in water (85 ml.) was treated with hypobromous acid (25 ml.) (prepared from 3.6 g. bromine in 100 ml. water), and barium carbonate (0.5 g.), and the mixture was stirred at 25° for 20 hours. The reaction mixture was concentrated in vacuo, and the residue was chromatographed on silica gel using 12% methanol in chloroform as the eluent to give 1,3,3'-tri-N-acetyl-5-O-acetylgaramine (0.66 g.) (41%) as a colorless amorphous solid with physical characteristics identical with those described in (i) above.

EXAMPLE 17

1,3,2',6',3''-Penta-N-acetyl-5,2'',4''-tri-O-acetylsisomicin

Sisomicin (600 mg.) in dry pyridine (60 ml.) was treated with acetic anhydride (12 ml.), and the mixture was heated under reflux for sixteen hours. The mixture was diluted with methanol, and allowed to stand at 25° for 2 hours. It was then concentrated in vacuo, and azeotroped with toluene until free of pyridine, and the residue was chromatographed on silica gel using 20% methanol in chloroform as the eluent to give 1,3,2',6',3''-penta-N-acetyl-5,2'',4''-tri-O-acetylsisomicin (100 mg.) (10%) as a colorless amorphous solid, (Found: C, 48.47; H, 6.50; N, 7.43. $C_{35}H_{53}N_5O_{15}$ requires : C, 53.63; H, 6.82; N, 8.94%), m/e 783 (M+), $[\alpha]_D^{26}$ + 77.5° ($CH_3OH$), $\nu$max (nujol) 3300, 1750, 1650, 1550, 1230, 1050 cm.$^{-1}$, $\delta(CD_3OD)$ † 1.36, 1.44 (3H, s, 4''-$CH_3$), 1.88–2.25 (24H, singlets, NAc, and OAc), 2.85, and 2.99 ppm. (3H, s, 3''—N—$CH_3$), $\delta$ (DMSO at 120°) 1.31 (3H, s, 4''-$CH_3$), 1.65 (6H, s, NAc, and/or OAc), 1.75 (3H, s, NAc, and/or OAc), 1.76 (3H, s, NAc, and/or OAc), 1.89 (3H, s, NAc, and/or OAc), 1.91 (3H, s, NAc, and/or OAc), 1.93 (6H, s, NAc, and/or OAc), 2.75 (3H, s, 3'—$NCH_3$), 5.05 (1H, d, $J_{1'',2''}$=2.5Hz, $H_{1''}$), and 5.25 ppm. (1H, broad s, $H_{1'}$), and 1,3,2',6',3''-penta-N-acetyl-5,2''-di-O-acetylsisomicin (390 mg.) (47%) as a colorless amorphous solid.

EXAMPLE 18

1,3,2',6',3''-Penta-N-(2,4-dinitrophenyl)-sisomicin

Sisomicin (2 g.), sodium bicarbonate (3 g.), and 2,4-dinitrofluorobenzene (8 g.) were dissolved in acetone-water (3:1) (50 ml.), and the mixture was stirred at 25° for 16 hours. The reaction mixture was evaporated to dryness in vacuo, and the residue was extracted repeatedly with tetrahydrofuran, and acetone, and the insoluble inorganic salts were filtered off. Evaporation of the combined filtrates, followed by chromatography on silica gel using 30% acetone in chloroform as the eluent gave a yellow solid which was washed with methanol affording 1,3,2',6',3''-penta-N-(2,4-dinitrophenyl)-sisomicin (5 g.) (88%) as a yellow amorphous solid, m.p. 195°–203°, (Found: C, 45.82; H, 3.71; N, 16.62. $C_{49}H_{47}N_{15}O_{27}$ requires: C, 46.20; H, 3.68; N, 16.50%), $[\alpha]_D^{26}$ + 90.0° (acetone), $\lambda$max (acetone) 351 m$\mu$ ($\epsilon$75,600), $\nu$max (nujol) 3330, 1630, 1590, 1050 cm.$^{-1}$.

EXAMPLE 19

1,3,3'-Tri-N-(2,4-dinitrophenyl)-garamine (i) 1,3,2',6',3''-Penta-N-(2,4-dinitrophenyl)-sisomicin (1 g.) was dissolved in tetrahydrofuran (50 ml.), and concentrated sulphuric acid was added until the pH reached 1. The solution was allowed to remain at 25° for 90 hours, and was then neutralized with lead carbonate, filtered, and evaporated to give a residue which was chromatographed on silica gel plates using first 4% methanol in chloroform, and then 8% methanol in chloroform as the eluent, to give 1,3,3'-tri-N-(2,4-dinitrophenyl)-garamine (133 mg.) (21%) as a yellow amorphous solid, with physical characteristics identical to those described in (ii) below and 1,3-di-N-(2,4-dinitrophenyl)-2-deoxystreptamine (181 mg.) (47%) as a yellow amorphous solid.

ii. Garamine (100 mg.), sodium bicarbonate (250 mg.), and 2,4-dinitrofluorobenzene (500 mg.) were dissolved in acetone-water (3:1) (10 ml.), and the mixture was stirred at 25° for 16 hours. The reaction mixture was evaporated to dryness, extracted with ethyl acetate, filtered to remove the inorganic salts, and the filrate was evaporated. The residue was chromatographed on silica gel plates using 25% methanol in chloroform as the eluent to give 1,3,3'-tri-N-(2,4-dinitrophenyl)-garamine (256 mg.) (100%) as a yellow amorphous solid, m.p. 192°–205°, (Found: C, 45.23; H, 4.34; N, 14.21. C$_{31}$H$_{33}$N$_9$O$_{18}$ requires: C, 45.4; H, 4.03; N, 15.40%), [α]$_D^{26}$ + 5.6° (acetone), λ max (acetone) 356 mμ (ε42,300), ν max (nujol) 3400, 1630, 1590, 1050 cm.$^{-1}$ δ(CD$_3$COCD$_3$) † 1.18, 1.31, (3H, s, 4'—CH$_3$), 2.82, 2.89 (3H, s, 3'—NCH$_3$), 5.50 (1H, d J$_{1',2'}$=3Hz, H$_1'$), and 7.35–9.00 ppm. (9H, complex groups of multiplets, aromatic H).

iii. 1,3,2',6',3''-Penta-N-(2,4-dinitrophenyl)-sisomicin (500 mg.) sodium carbonate (1 g.), and m-chloroperbenzoic acid (4.5 ml.) were dissolved in tetrahydrofuran (22 ml.) containing water (0.5 ml.), and the mixture was stirred at 25° for 7 days. The mixture was evaporated to small volume, taken up in chloroform, and shaken with 10% aqueous sodium sulphite, and then with aqueous sodium bicarbonate, and finally water. The chloroform was dried (MgSO$_4$), evaporated, and the residue chromatographed on silica gel plates using 20% methanol in chloroform as the eluent to give 1,3,3'-tri-N-(2,4-dinitrophenyl)-garamine (194 gm.) (60%) as a yellow amorphous solid which was identical with that described in (i), and (ii) above.

EXAMPLE 20

2'-O-Benzyl-1,3-di-N-carbobenzoxy-4,5-O-isopropylidene-garamine-3',4'-oxazolidinone 1,3,3'-Tri-N-carbobenzoxy-4,5,-O-isodpropylidenegaramine (1 g.) was dissolved in anhydrous dimethylformamide (16 ml.) and barium oxide (1.05 g.) and barium hydroxide (1.25 g.) were added. The mixture was stirred and cooled to − 10° and benzyl bromide (0.75 ml.) was added dropwise. The mixture was allowed to warm up to room temperature and after 24 hours the solution was diluted with chloroform and filtered. The filtrate was evaporated to dryness and the resulting gum solidified on trituration with water. Chromatography on silica gel plates using 7% methanol in chloroform as the eluent gave 2'-O-benzyl-1,3-di-N-carbobenzoxy-4,5-O-isopropylidene-garamine-3',4'-oxazolidinone (0.26 g.) as a colorless amorphous solid, (Found: C, 63.18; H, 6.28; N, 5.97. C$_{40}$H$_{47}$N$_3$O$_{11}$ requires: C, 64.40; H, 6.31; N, 5.64%), [α]$_D^{26}$ + 63.8° (C$_2$H$_5$OH), λ max (CH$_3$OH) 208 mμ (ε23,800), ν max (CHCl$_3$) 3400, 3300, 1730, 1200 cm.$^{-1}$, δ(CDCl$_3$) † 1.24, 1.40 (9H, broad singlets, 4'—CH$_3$ and

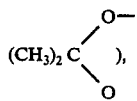

2.78 (3H, broad s, 3'—NCH$_3$), 7.22 and 7.27 ppm (15H, singlets, aromatic protons).

EXAMPLE 21

2'-O-Benzyl-1,3-di-N-carbobenzoxygaramine-3',4'-oxazolidinone

2'-O-Benzyl-1,3-di-N-carbobenzoxy-4,5-O-isopropylidenegaramine-3',4'-oxazolidinone (0.15 g.) was dissolved in 80% aqueous acetic acid (5 ml.) and the solution was allowed to remain at 25° for 16 hours. The solution was evaporated to dryness to give 2'-O-benzyl-1,3-di-N-carbobenzoxygaramine-3',4'-oxazolidinone (102 mg) as a colorless amorphous solid, (Found: C, 62.68; H, 6.20; N, 5.93. C$_{37}$H$_{43}$N$_3$O$_{11}$ requires: C, 63.00; H, 6.10; N, 5.96%), [α]$_D^{26}$ + 53.6° (CHCl$_3$) λ max (CH$_3$OH) 208 mμ (ε24,800), ν max (CHCl$_3$) 3400, 1740, 1720, 1200 cm.$^{-1}$, δ(CDCl$_3$) † 1.28 (3H, broad s, 4'—CH$_3$), 2.54 (3H, broad s, 3'—NCH$_3$), 5.05 (4H, broad s, C$_6$H$_5$CH$_2$OCO—), 7.26 and 7.29 ppm (10H, singlets, C$_6$H$_5$OC̄Ō—).

EXAMPLE 22

Gentamicin X$_2$ i. 1,3,3'-Tri-N-carbobenzoxygaramine (20 g.), and 3,4,6-tri-O-acetyl-2-deoxy-2-nitroso-α-D-glucopyranosyl chloride (9.34 g.) were dissolved in dry, redistilled dimethylformamide (200 ml.), and the solution was allowed to remain at 25° for 88 hours. The solution was concentrated in vacuo, and was dried (MgSO$_4$), filtered, and evaporated to give the crude product. Chromatography on a silica gel column (160 × 5 cm.) using 3% methanol in chloroform as the eluent gave O-[3,4,6-tri-O-acetyl-2-deoxy-2-oximino-α-D-glucopyranosyl-(1→4)]-1,3,3'-tri-N-carbobenzoxy-garamine (8.2 g.) as a colorless amorphous solid, m.p. 171°–173°, (Found: C, 56.97; H, 5.91; N, 5.65. C$_{49}$H$_{60}$N$_4$O$_{20}$ requires: C, 57.41; H, 5.90; N, 5.47%), [α]$_D^{26}$ + 86.7° (CH$_3$OH), ν max (CHCl$_3$) 3380, 1750, 1720, 1230, 1030, 694 cm.$^{-1}$, δ(CDCl$_3$) † 1.01 (3H, broad s, 4''—CH$_3$), 1.95 (9H, broad s, OAc), 3.02 (3H, broad s, 3''—NCH$_3$), 5.02 (6H, broad s, —CH$_2$C$_6$H$_5$), and 7.24 ppm. (15H, broad s, —CH$_2$C$_6$H$_5$).

O-[3,4,6-Tri-O-acetyl-2-deoxy-2-oximino-α-D-glucopyranosyl-(1→4)]-1,3,3'-tri-N-carbobenzoxygaramine (1 g.), and acetic anhydride (1.5 ml.) were dissolved in dry pyridine (4 ml.), and the solution was allowed to remain at 25° for 16 hours. The reaction mixture was poured into ice-water, and the solid O-[2,3,4,6-tetra-O-acetyl-2-deoxy-2-oximino-α-D-glucopyranosyl-(1→4)]-1,3,3'-tri-N-carbobenzoxy-garamine was filtered off, and dried. The acetate was dissolved in dry tetrahydrofuran (25 ml.) and cooled to 0°. A 1 M solution of diborane in tetrahydrofuran (18.7 ml.) was added and the mixture was allowed to remain at 25° for 16 hours. Excess reagent was destroyed by careful addition of water, and when no further effervescence occurred a saturated solution of ammonia in methanol (100 ml.) was added, and the solution was allowed to remain at 25° until complete removal of the acetates had been effected. The solution was evaporated in vacuo, and the residue was taken up in glacial acetic acid and hydrogenated over 30% palladium on carbon at 25° at 55 p.s.i. for 18 hours. The catalyst was filtered off, and the filtrate after evaporation was heated under reflux with hydrazine hydrate for 17 hours. Evaporation in vacuo followed by chromatography of the residue on a silica gel column using the lower phase of a chloroform-methanol-ammonium hydroxide solution (1:1:1) as the eluent, gave gentamicin X$_2$ (84 mg.) which after passage down Amberlite IR 401S resin and lyophilization was obtained as a colorless amorphous solid, (Found: C, 44.98; H, 7.77; N, 11.00. C$_{19}$H$_{38}$N$_4$O$_{10}$.H$_2$O requires: C, 45.60; H, 8.00; N, 11.20%), m/e 483 (M$^+$ + 1), [α]$_D^{26}$ + 158.8° (H$_2$O), ν max (KCl) 3350, 1040 cm.$^{-1}$, δ(D$_2$O) 1.19 (3H, s, 4''—CH$_3$), 2.49 (3H, s, 3''—NCH$_3$), 5.08 (1H, d, J=4Hz, H$_{1''}$), and 5.22 ppm. (1H, d, J = 4Hz, H$_{1'}$), [θ]$_{290}$ - 12,500 (TACu).

ii. 2'-O-Acetyl-1,3,3'-tri-N-carbobenzoxygaramine (0.91 g.), and 3,4,6-tri-O-acetyl-2-deoxy-2-nitroso-α-D-glucopyranosyl chloride (0.61 g.) were dissolved in dry, redistilled dimethylformamide (4 ml.), and the solution was allowed to remain at 25° for 115 hours. The solution was concentrated in vacuo, and partitioned between chloroform, and water. The chloroform extract was dried (MgSO$_4$), filtered, and evaporated to give the crude product. Chromatography on a silica gel column (60 × 2.5 cm.) using 3% methanol in chloroform as the eluent gave O-[3,4,6-tri-O-acetyl-2-deoxy-2-oximino-α-D-glucopyranosyl-(1→4)]-2'-O-acetyl-1,3,3'-tri-N-carbobenzoxy-garamine (0.53 g.) as a colorless amorphous solid, m.p. 116°-127°, (Found: C, 56.71; H, 5.96; N, 5.31. C$_{51}$H$_{62}$N$_4$O$_{21}$ requires: C, 57.39; H, 5.82; N, 5.26%), $[\alpha]_D^{26}$ + 92.6° (C$_2$H$_5$OH), $\nu$ max (CHCl$_3$) 3330, 1740, 1700, 1210, 1045, 1030, 696 cm.$^{-1}$, δ(CDCl$_3$) † 1.03 (3H, broad s, 4''—CH$_3$), 1.91-2.17 (12H, broad s, OAc), 2.90 (3H, broad s, 3''—NCH$_3$), and 7.21-7.29 ppm. (15H, broad s, —CH$_2$C$_6$H$_5$).

The oxime was converted to the acetate, reduced with diborane, deblocked, and chromatographed as in (i) above to give gentamicin X$_2$ as a colorless amorphous solid (60 mg.).

iii. 5,2',4'-Tri-O-acetyl-1,3,3'-tri-N-carbobenzoxy garamine (9.17 g.), 3,4,6-tri-O-acetyl-2-deoxy-2-nitroso-α-D-glucopyranosyl chloride (7.33 g.) and N,N,2,6-tetramethylaniline (1.5 g.) were dissolved in dry, redistilled dimethylformamide (300 ml.) and the solution was allowed to stand at 25° for 95 hours. The reaction mixture was poured into ice-water (5 liters and the precipitate was filtered, dried, and chromatographed on a silica gel column (160 × 5 cm.) using 1% methanol in chloroform as the eluent, to give O-[3,4,6-tri-O-acetyl-2-deoxy-2-oximino-α-D-glucopyranosyl-(1→4)]-5,2',4'-tri-O-acetyl-1,3,3'-tri-N-carbobenzoxy-garamine (5.0 g.) as a colorless amorphous solid, m.p. 134°-139°, (Found: C, 57.61; H, 5.88; N, 4.79. C$_{55}$H$_{66}$N$_4$O$_{23}$ requires: C, 57.38; H. 5.78; N, 4.87%), $[\alpha]_D^{26}$ + 90.0° (CH$_3$OH), $\nu$ max (CHCl$_3$) 3350, 1740, 1710, 1220, 1030, 695 cm.$^{-1}$ δ(CDCl$_3$) † 1.29, 1.39 (3H, broad s, 4''—CH$_3$), 1.99 (18H, broad s, OAc), 2.85 (3H, broad s, 3''—NCH$_3$), 5.08 (6H, broad s, —CH$_2$C$_6$H$_5$), 6.19 (1H, broad s, H$_{1'}$), and 3.28 ppm. (15H, broad s, —CH$_2$C$_6$H$_5$).

O-[3,4,6-Tri-O-acetyl-2-deoxy-2-oximino-α-D-glucopyranosyl-(1→4)]-5,2',4'-tri-O-acetyl-1,3,3'-tri-N-carbobenzoxygaramine (1.0 g.), and acetic anhydride (1.5 ml.) were dissolved in dry pyridine (15 ml.) and the solution was allowed to remain at 25° for 17 hours. The reaction mixture was poured into ice-water, and the solid O-[2,3,4,6-tetra-O-acetyl-2-deoxy-2-oximino-α-D-glucopyranosyl-(1→4)]-5,2',4'-tri-O-acetyl-1,3,3'-tri-N-carbobenzoxygaramine (828 mg.) was filtered off and dried. The acetate was chromatographed on a silica gel column (110 × 2.5 cm.) using 1% methanol in chloform as the eluent to give an analytical sample as a colorless amorphous solid, m.p. 115°14 123°, (Found: C, 57.36; H, 5.96; N, 4.66. C$_{57}$H$_{68}$N$_4$O$_{24}$ requires: C, 57.38; H, 5.75; N, 4.70%), $[\alpha]_D^{26}$ + 88.0° (CH$_3$OH), $\nu$ max (CHCl$_3$), 5338, 1740, 1710, 1220, 1030, 695 cm.$^{-1}$, δ(CDCl$_3$) † 1.27, 1.37 (3H, broad s, 4''—CH$_3$), 1.92, 2.01, 2.09, 2.17 (21H, broad s, OAc), 2.85 (3H, broad s, 3''—NCH$_3$) 5.07 (6H, broad s, —CH$_2$C$_6$H$_5$), and 3.31 ppm. (15H, broad s, —CH$_2$C$_6$H$_5$).

The acetate (386 mg.) was dissolved in dry tetrahydrofuran (10 ml.) and cooled to 0°. A 1M solution of diborane in tetrahydrofuran (6.67 ml.) was added dropwise with stirring and the mixture was kept at 7° for 18 hours. Excess reagent was destroyed by dropwise addition of water until no further effervescence occurred. The solution was evaporated, and azeotroped with benzene to give the product as a dry, amorphous solid. The latter was added to a mixture of sodium (0.66 g.) in liquid ammonia (40 ml.) at −70° and the mixture was stirred for two hours. The reaction was quenched by dropwise addition of water, and the ammonia was allowed to evaporate at 25° overnight. The buff-colored residue was dissolved in ice-cold water (70 ml.) and neutralized with pre-washed Amberlite IRC 50 resin. After two hours, the resin slurry was transferred to a column and washed with water (approximately 1.5 liters), followed by elution of the gentamicin X$_2$ with 1.5N ammonium hydroxide. The basic eluate was evaporated to dryness and the resulting glass was chromatographed on a silica gel column (110 × 2.5 cm.) using the lower phase of a chloroform-methanol-ammonium hydroxide solution (1:1:1) as the eluent. The gentamicin X$_2$ was collected, passed down Amberlite IR401S resin and lyophilized to give a colorless amorphous solid (34 mg.), having identical physical properties as described in (i) above.

iv. O-[2,3,4,6-Tetra-O-acetyl-2-deoxy-2-oximino-α-D-glucopyranosyl-(1→4)]-5,2',4'-tri-O-acetyl-1,3,3'-tri-N-carbobenzoxygaramine (450 mg.) was dissolved in dry tetrahydrofuran (12 ml.) and cooled to 0°. A 1M solution of diborane in tetrahydrofuran (7.75 ml.) was added dropwise and the mixture was kept at 7° for 18 hours. Excess reagent was destroyed by dropwise addition of water until no further effervescence occurred. The solution was evaporated and azeotroped with benzene to give the product as a dry amorphous solid. The latter was taken up in glacial acetic acid (70 ml.) and hydrogenated over 30% Pd on carbon at 25°, 55 p.s.i. for 17 hours. The catalyst was filtered off, washed with water, and the filtrate was evaporated to dryness and azeotroped with benzene. The residue and barium hydroxide (5 g.) were dissolved in water (50 ml.) and the solution was heated under reflux at 130° for 16 hours. The solution was cooled, saturated with carbon dioxide and the barium carbonate was filtered off and washed with water. The filtrate was passed down Amberlite IR401S resin and the eluate was evaporated and chromatographed on a silica gel column (110 × 2.5 cm.) using the lower phase of a chloroform-methanol-ammonium hydroxide solution (1:1:1) as the eluent, to give gentamicin X$_2$ (24 mg.) as a colorless amorphous solid after lyophilization, having identical physical properties with that prepared in (i) above.

v. O-[2,3,4,6-Tetra-O-acetyl-2-deoxy-2-oximino-α-D-glucopyranosyl-(1→4)]-5,2',4'-tri-O-acetyl-1,3,3'-tri-N-carbobenzoxygaramine (500 mg.) in dry tetrahydrofuran (500 mg.) in dry tetrahydrofuran (20 ml.) was reduced with 1M diborane in tetrahydrofuran (4.18 ml.) as in (iv) above. The reduction product was taken up in aqueous dioxane (1:1) (40 ml.) containing barium hydroxide (2 g.) and was heated under reflux at 130° for 17 hours. The solution was neutralized with Amberlite IRC 50 resin and the slurry was poured onto a column. The resin was washed with water and the gentamicin X$_2$ was then eluted with 1.5M ammonium hydroxide. The basic eluate was evaporated to dryness, chromatographed on a silica gel column (110 × 2.5 cm.) as before to give gentamicin X$_2$ (50 mg.). The product was identical with that prepared in (i) above.

vi. O-[2,3,4,6-Tetra-O-acetyl-2-deoxy-2-oximino-α-D-glucopyranosyl-(1→4)]5,2',4'-tri-O-acetyl-1,3,3'-tri-N-carbobenzoxygaramine (500 mg.) in dry tetrahydrofuran (20 ml.) was reduced with 1M diborane in tetrahydrofuran (4.18 ml.) as in (iv) above. The reduction product was taken up in aqueous dioxane (1:1) (40 ml.) containing sodium hydroxide (2 g.) and was heated under reflux at 130° for 17 hours. The reaction was worked-up as in (v) above to give gentamicin $X_2$ (90 mg.). The product was identical with that prepared in (i) above.

vii. 2'-O-Acetyl-1,3,3'-tri-N-carbobenzoxygaramine (1.5 g.) in dry toluene (100 ml.) was treated with Drierite (freshly ground and baked out on a hotplate (8.6 g.), mercuric cyanide (0.83 g.) and 3,4,6-tri-O-acetyl-2-amino-2-deoxy-2-N-(2,4-dinitrophenyl)-α-D-glucopyranosyl bromide (1.25 g.), and the mixture was heated at 110° for 24 hours. The solution was cooled, filtered through a celite pad, and the filtere cake was washed with ethyl acetate. The combined filtrates were evaporated, taken up in ethyl acetate (300 ml.), and washed with 20% potassium bromide (3 × 100 ml.), water (3 × 100 ml.), dried (MgSO$_4$), filtered, and evaporated. Chromatography on a silica gel (100 g.) column using 1% methanol in benzene-ether (1:1) gavie O-[3,4,6-tri-O-acetyl-2-amino-2-deoxy-2-N-(2,4-dinitrophenyl)-α-D-glucopyranosyl-(1→4)]-2'-O-acetyl-1,3,3'-tri-N-carbobenzoxygaramine (838 mg.) which crystallized from 95% ethanol-water, m.p. 128°–130°, (Found: C, 56.48; H, 5.17; N, 6.88. $C_{57}H_{66}N_6O_{24}$ requires: C, 56.16; H, 5.46; N, 6.89%), $[\alpha]_D^{26}$ + 98.0° (CHCl$_3$), ν max (nujol) 3448, 3333, 1754–1709, 1618, 1592, 1527 cm.$^{-1}$, δ(CDCl$_3$—CD$_3$OD, 3:1) † 1.18 (3H, broad s, 4"—CH$_3$), 1.85, 2.02, 2.08 (12H, broad s, OAc), 2.95 (3H, broad s, 3"—NCH$_3$), 7.33, 7.38 (16H, broad s, —CH$_2$C$_6$H$_5$ and DNP), and 8.25, 9.03 ppm. (2H, broad DNP). Further elution of the column with 2% methanol in benzene-ether (1:1) gave a mixed cut which was further purified by preparative t.l.c. on silica gel plates using chloroform-ethyl acetate (1:2) as the eluent, to give O-[3,4,6-tri-O-acetyl-2-amino-2-deoxy-2-N-(2,4-dinitrophenyl)-β-D-glucopyranosyl-(1→4)]-2'-O-acetyl-1,3,3'-tri-N-carbobenzoxygaramine (150 mg.) which crystallized from 95% ethanol-water, m.p. 133°–135°, (Found: C, 56.96; H, 5.65; N, 6.79. $C_{57}H_{66}N_6O_{24}$ requires: C, 56.16; H, 5.46; N, 6.89%), $[\alpha]_D^{19}$ + 39.5° (CHCl$_3$), ν max (nujol) 3448, 3333, 1754–1709, 1618, 1592, 1527 cm.$^{-1}$, δ(CDCl$_3$) † 1.10 (3H, broad s, 4"-CH$_3$), 1.88, 2.03, 2.10 (12H, broad s, OAc), 2.92 (3H, broad s, 3"-NCH$_3$), 7.25, 7.28, 7.30, 7.33 (16H, broad s, —CH$_2$C$_6$H$_5$ and DNP), and 8.20, 9.00 ppm. (2H, broad, DNP).

O-[3,4,6-Tri-O-acetyl-2-amino-2-deoxy-2-N-(2,4-dinitrophenyl)-α-D-glucopyranosyl-(1→4)]-2'-O-acetyl-1,3,3'-tri-N-carbobenzoxygaramine (160 mg.) was dissolved in methanol (32 ml.), and the solution was saturated with ammonia at 0°. After 16 hours at 25° the solution was evaporated to afford 1,3,3"-tri-N-carbobenzoxy-2'-N-(2,4-dinitrophenyl)-gentamicin $X_2$ which was dissolved in a mixture of acetone (20 ml.), and water (10 ml.), and treated with Amberlite IRA 400 ion exchange resin (OH$^-$ form) (5 ml.), and stirred at 25° for 16 hours. The mixture was filtered, and the resin was washed with acetone-water (2:1) (100 ml.), and the combined filtrates were evaporated to afford 1,3,3"-tri-N-carbobenzoxygentamicin $X_2$. The latter was dissolved in liquid ammonia (20 ml.) at −70° (dry ice-acetone bath), and sodium (230 mg.) was added. The blue solution was stirred at −70° for 2 hours. Water was added dropwise until the blue color discharged. The ammonia was allowed to evaporate, and the residue was taken up in water (5 ml.). The aqueous solution was cooled to 0°, and transferred onto an Amberlite IRC 50 ion exchange column, and allowed to stand for 1½ hours. The neutral impurities were eluted with water (140 ml.), and the gentamicin $X_2$ (36 mg.) was then eluted with 1.5 N ammonium hydroxide. The product of this reaction was identical to that described in (i) above.

EXAMPLE 23

2'-N-Ethylgentamicin $X_2$

2'-N-Ethylgentamicin $X_2$ (formed as a by-product in the preparation of gentamicin $X_2$ in (VI) above, which was rechromatographed on a silica gel column (110 × 2.5 cm.) using same eluent as above to give a colorless solid (5 mg.) after passage down Amberlite IR401S and lyophylization, m/e 510 (M$^+$), δ(D$_2$O) 1.02 (3H, t, J = 7Hz, C$\underline{H_3}$CH$_2$NH—), 1.16 (3H, s, 4"—CH$_3$), 2.46 (3H, s, 3"—NC$\underline{H_3}$), 2.53 (1H, d, J = 10.5Hz, H$_3$"), 2.71 (2H, q, J = 7Hz, CH$_3$C$\underline{H_2}$NH—), 3.26 (1H, d, J = 12Hz, H$_5$), 4.07 (1H, d, J = 12Hz, H$_5$), 5.03 (1H, d, J = 4Hz, H$_1$") and 5.15 ppm (1H, d, J = 3.5Hz, H$_1$'), [θ]$_{290}$ - 6,010 (TACu).

EXAMPLE 24

4,6-Di-O-acetyl-2,3-dideoxy-2-nitroso-α-D-glucopyranosyl chloride 4,6-Di-O-acetyl-1,2,3-trideoxy-D-erythrohex-1-enopyranose (41.7 g.) was dissolved in dry ethyl acetate (1250 ml.) and the solution was flushed with dry nitrogen and cooled to 0°. A solution of nitrosyl chloride (25.5 g./100 ml.) in dry ethyl acetate was added and the mixture was allowed to remain at −5° for 2 hours and 45 minutes at which time the reaction was found to be complete by thin layer chromatography. The solution was evaporated to dryness and the gum was triturated with dry ether and then dried under vacuum to give 4,6-di-O-acetyl-2,3-dideoxy-2-nitroso-α-D-glucopyranosyl chloride (54 g.) as a colorless glass, (Found: C, 42.91; H, 5.10; N, 4.83; Cl 12.75. $C_{10}H_{14}NO_6Cl$ requires: C, 42.94; H, 5.05; N, 5.01; Cl, 12.68%), $[\alpha]_D^{26}$ + 75.5° (CHCl$_3$), ν max (CHCl$_3$) 1740, 1220, 1040 cm.$^{-1}$, δ(CDCl$_3$) 2.10 (6H, s, OAc), and 6.70, 6.82 ppm (1H, d, J = 4Hz) (3:2).

EXAMPLE 25

3'-Deoxygentamicin $X_2$ 5,2',4'-Tri-O-acetyl-1,3,3'-tri-N-carbobenzoxygaramine (7.28 g.) and 4,6-di-O-acetyl-2,3-dideoxy-2-nitroso-α-D-glucopyranosyl chloride (4.8 g.) were dissolved in dry, redistilled dimethylformamide (200 ml.) and the solution was allowed to stand at 25° for 46 hours. The reaction mixture was poured into ice-water and the precipitate was filtered, dried and chromatographed on a silica gel column (160 × 2.5 cm.) using 1% methanol in chloroform as the eluent, to give O-[4,6-di-O-acetyl-2,3-dideoxy-2-oximino-α-D-glucopyranosyl-(1→4)]-5,2',4'-tri-O-acetyl-1,3,3'-tri-N-carbobenzoxygaramine (4.8 g.) as a colorless amorphous solid, m.p. 123°–133°, (Found: C, 58.01; H, 5.72; N, 5.02. $C_{53}H_{64}N_4O_{21}$ requires: C, 58.23; H, 5.90; N, 5.13%), $[\alpha]_D^{26}$ + 117.0° (CH$_3$OH), νmax (CHCl$_3$) 3400, 1740, 1710, 1220, 1030, 695 cm.$^{-1}$, δ(CDCl$_3$) † 1.25, 1.37 (3H, broad s, 4"—CH$_3$), 1.90, 1.96, 2.01 (15H, broad s, OAc), 2.83 (3H, broad s, 3"—NCH$_3$), 5.07 (6H, broad s, —CH$_2$C$_6$H$_5$), and 7.28 ppm. (15H, broad s, —CH$_2$C$_6$H$_5$).

O-[4,6-di-O-acetyl-2,3-dideoxy-2-oximino-α-D-glucopyranosyl-(1→4)]-5,2',4'-tri-O-acetyl-1,3,3'-tri-N-carbobenzoxygaramine (3.3 g.), and acetic anhydride (4.9 ml.) were dissolved in dry pyridine (26 ml.) and the solution was allowed to remain at 25° for 18 hours. The reaction mixture was poured into water and the solid O-[2,4,6-tri-O-acetyl-2,3-dideoxy-2-oximino-α-D-glucopyranosyl-(1→4)]-5,2',4'-tri-O-acetyl-1,3,3'-tri-N-carbobenzoxygaramine (3.2 g.) was filtered off and dried.

The acetate (3.2 g.) was dissolved in dry tetrahydrofuran (100 ml.) and cooled to 0°. A 1M solution of diborane in tetrahydrofuran (42.3 ml.) was added dropwise and the mixture was kept at 7° for 18 hours. Excess reagent was destroyed by dropwise addition of water until no further effervescence occurred. The solution was evaporated and azeotroped with benzene to give the product as a dry amorphous solid. The latter was taken up in aqueous dioxane (1:1) (160 ml.) containing sodium hydroxide (8 g.) and was heated under reflux at 130° for 17 hours. The solution was neutralized with Amberlite IRC 50 resin and the slurry was poured into a column. The resin was washed with water and the 3'-deoxygentamicin $X_2$ was then eluted with 1.5M ammonium hydroxide. The basic eluate was evaporated to dryness and chromatographed on a silica gel column (160 × 2.5 cm.) using chloroform-methanol-7% ammonium hydroxide (15:27:15) as the eluent to give 3'-deoxygentamicin $X_2$ which after passage down Amberlite IR401S resin and lyophilization was obtained as a colorless amorphous solid (0.8 g.), m.p. 131°–141°, (Found: C, 48.72; H, 8.08; N, 11.92. $C_{19}H_{38}N_4O_9$ requires: C, 48.91; H, 8.21; N, 12.01%), m/e 467 M+ + 1), $[\alpha]_D^{26}$ + 171.6° (H$_2$O), νmax (KCl) 3340, 1030 cm.$^{-1}$, δ(D$_2$O) 1.14 (3H, s, 4"—CH$_3$), 2.45 (3H, s, 3"—NCH$_3$), 5.01 (1H, d, J = 3.5Hz, H$_1$"), and 5.04 ppm (1H, d, J = 3Hz, H$_1$), $[\theta]_{290}$ - 9,040 (TACu), $[\theta]_{290}$ - 7,550 (Cupra A).

EXAMPLE 26

3'-Deoxygentamicin $X_2$ 1,3,3'-Tri-N-carbobenzoxygaramine (3.75 g.), and 4,6-di-O-acetyl-2,3-dideoxy-2-nitroso-α-D-glucopyranosyl chloride (1.8 g.) in dry, redistilled dimethylformamide (30 ml.) were stirred at 25° for 19 hours. The solution was concentrated in vacuo and then taken up in chloroform. The chloroform solution was washed with water, dried (MgSO$_4$), and evaporated and the residue was chromatographed on a silica gel column using 4% methanol in chloroform as the sluent. The O-[4,6-di-O-acetyl-2,3-didexoy-2-oximino-α-D-glucopyranosyl-(1→4)]-1,3,3'-tri-N-carbobenzoxygaramine (0.8 g.) was obtained as a colorless amorphous solid, m.p. 112°–119°, (Found: C, 58.68; H, 6.11; N, 5.76. $C_{47}H_{58}N_4O_{16}$ requires: C, 58.38; H, 6.05; N, 5.79%), $[\alpha]_D^{26}$ + 106.3° (C$_2$H$_5$OH), νmax (CHCl$_3$) 3330, 1740, 1710, 1220, 1055, 1030, 695 cm.$^{-1}$, δ(CDCl$_3$) + 1.00 (3H, broad s, 4"-CH$_3$), 1.92 (3H, broad s, OAc), 1.98 (3H, broad s, OAc), 2.99 (3H, broad s, 3"—NCH$_3$), 5.02 (6H, broad s, —CH$_2$C$_6$H$_5$), and 7.23 ppm. (15H, broad s, —CH$_2$C$_6$H$_5$).

The O-[4,6-di-O-acetyl-2,3-dideoxy-2-oximino-α-D-glucopyranosyl-(1→4)]-1,3,3'-tri-N-carbobenzoxygaramine (0.7 g.) was acetylated, reduced with diborane and the resulting product was deprotected by alkaline hydrolysis as in Example 1 above to give 3'-deoxygentamicin $X_2$ (70 mg.)

EXAMPLE 27

3'-Deoxygentamicin $X_2$

In addition to 3'-deoxygentamicin $X_2$, the process also give the 1,3-urea derivative of 3'-deoxygentamicin $X_2$ which after passage down Amberlite IR401S resin and lyophilization was obtained as a colorless amorphous solid (1.0 g.), Found: C, 47.62; H, 7.53; N, 11.13. $C_{20}H_{36}N_4O_{10} \cdot H_2O$ requires: C, 47.05; H, 7.50; N, 1097%), m/e 493 (M+ + 1), $[\alpha]_D^{26}$ + 171.6° (H$_2$O), νmax (KCl) 3330, 1660, 1060, 1030 cm$^{-1}$, δ(D$_2$O) 1.17 (3H, s, 4"-CH$_3$), 2.45 (3H, s, 3"-NCH$_3$), 4.86 (1H, d, J = 3.5Hz, H$_1$"), 4.96 ppm (1H, d, J = 4Hz, H$_1$).

The 1,3-urea derivative of 3'-deoxygentamicin $X_2$ (3.5 g.) was dissolved in hydrazine hydrate (50 ml.) and the mixture was heated in a bomb at 130° for 89 hours. The solution was evaporated in vacuo and the residue was repeatedly dissolved and evaporated from water and then methanol. The colorless solid was chromatographed on a silica gel column (160 × 2.5 cm.) using chloroform-methanol-7% ammonium hydroxide (1:2:1) as the eluent to give 3'-deoxygentamicin $X_2$ as a colorless amorphous solid after passage down Amberlite IR401S resin and lyophilization (1.56 g.).

EXAMPLE 28

3'-Deoxy-2'-N-ethylgentamicin $X_2$

3'-Deoxy-2'-N-ethylgentamicin $X_2$, (formed as a by-product in the preparation of 3'-deoxy-gentamicin $X_2$) was rechromatographed on a silica gel column (160 × 2.5 cm.) using the lower phase of a chloroform-methanol-ammonium hydroxide solution (1:1:1) as the eluent to give a colorless amorphous solid (254 mg.) after passage over Amberlite IR401S resin and lyophilization, (Found: C, 50.91; H, 8.41; N, 11.33%. $C_{21}H_{42}N_4O_9$ requires: C, 50.99; H, 8.56; N, 11.33%), m/e 495 (M+ + 1), $[\alpha]_D^{26}$ + 147.9° (H$_2$O), νmax (KCl) 3300, 1050 cm.$^{-1}$ δ(D$_2$O) 1.00 (3H, t, J = 7Hz, CH$_3$CH$_2$NH—), 1.17 (3H, s, 4"—CH$_3$), 2.47 (3H, s, 3"—NCH$_3$), 2.52 (1H, d, J = 10.5Hz, H$_3$"), 2.64 (2H, q, J = 7Hz; CH$_3$CH$_2$NH—), 3.28 (1H, d, J = 12.5Hz, H$_{5a}$"), 3.74 (1H, dd, J = 10.5Hz, J = 4Hz, H$_2$"), 4.07 (1H, d, J = 12.5Hz, H$_{5e}$"), 5.05 (1H, d, J = 4Hz, H$_1$") and 5.14 ppm (1H, d, J = 3.5Hz, H$_1$'), $[\theta]_{290}$ - 8,800 (TACu), $[\theta]_{290}$ - 7,280 (Cupra A).

EXAMPLE 29

O-α-D-Glucopyranosyl-(1→4)-garamine i. O-[3,4,6-Tri-O-acetyl-2-deoxy-2-oximino-α-D-glucopyranosyl-(1→4)]-5,2',4'-tri-O-acetyl-1,3,3'-tri-N-carbobenzoxygaramine (500 mg.) in glacial acetic acid (7 ml.) was treated with levulinic acid (1 g.) and 1N hydrochloric acid (1 ml.) and the mixture was stirred at 25° for 18 hours. The mixture was extracted with methylene chloride and the latter extract was washed with aqueous sodium bicarbonate, water and was dried over magnesium sulphate. The solution was evaporated and the solid was dissolved in dioxan (10 ml.) containing water (1 ml.) and cooled to 5°. Sodium borohydride (100 mg.) in dioxan (2 ml.) and water (4 ml.) was added dropwise with stirring. Stirring was maintained at 5° for one half hour and at 25° for 1 hours. The reaction was quenched with acetic acid and evaporated to dryness. The residue was dissolved in liquid ammonia (80 ml.) at −70° and sodium (1 g.) was added. After stirring at −70° for three hours, the reaction was quenched by dropwise addition of water and the ammonia was allowed to evaporate overnight. The residue was taken up in water and added to Amberlite IRC 50 resin (200 g.) and allowed to stand for two hours. The resin slurry was transferred to a column and after first washing with water, the product was eluted with 1.5N ammonium hydroxide solution. The basic eluate was evaporated and the residue chromatographed on a silica gel column (160 × 2.5 cm.) using chloroform-methanol-7% ammonium hydroxide solution (1:2:1) as the eluent to give O-α-D-glucopyranosyl-(1→4)-garamine (39 mg.) as a colorless amorphous solid after passage down Amberlite IR401S resin and lyophilization, (Found: C, 46.93; H, 7.82; N, 8.87. $C_{19}H_{37}N_3O_{11}$ requires: C, 47.19; H, 7.71; N, 8.69%), m/e 484 (M+. + 1), $[\alpha]_D^{26}$ + 146.3° ($H_2O$), νmax (KCl) 3300 1050 cm.$^{-1}$, δ($D_2O$) 1.16 (3H, s, 4″—$CH_3$), 2.47 (3H, s, 3″—$NCH_3$), 5.01 (1H, d, J = 4Hz, $H_1$″), and 5.12 ppm. (1H, d, J = 3.5Hz, $H_1$′), $[\theta]_{290}$ - 7,380 (TACu).

ii. O-[3,4,6-Tri-O-acetyl-2-deoxy-2-oximino-α-D-glucopyranosyl-(1→4)]-5,2′,4′-tri-O-acetyl-1,3,3′-tri-N-carbobenzoxygaramine (500 mg.) was dissolved in dioxan (10 ml.). Solid ammonium acetate (5 g.) and 50% aqueous acetic acid (2 ml.) were added and the mixture was stirred under nitrogen. Titanium trichloride (20% solution) (12 ml.) was added gradually and the mixture was stirred at 25° for 1 hour. Water was added and the reaction mixture was extracted three times with chloroform. The chloroform extract was washed with water, dried ($MgSO_4$) and evaporated to dryness. The residue was taken up in a mixture of dioxan (10 ml.) and water (1 ml.) was cooled to 5°. Sodium borohydride (100 mg.) in dioxan (2 ml.) and water (4 ml.) was added slowly with stirring. The mixture was stirred at 5° for a half hour and at 25° for 1 hour, and excess hydride was destroyed by dropwise addition of acetic acid. The solution was evaporated to dryness and treated with sodium in liquid ammonia as in (i) above to give O-α-D-glucopyranosyl-(1→4)-garamine (14 mg.) which was identical with that prepared in (i) above.

iii. O-[3,4,6-Tri-O-acetyl-2-deoxy-2-oximino-α-D-glucopyranosyl-(1→4)]-5,2′,4′-tri-O-acetyl-1,3,3′-tri-N-carbobenzoxygaramine (500 mg.) was dissolved in glyme (10 ml.) and water (6 drops) and 70% perchloric acid (8 drops) were added. Thallium (III) nitrate (1.5 g.) in glyme (10 ml.) was added with stirring and the mixture was stirred at 25° for 19 hours. The mixture was diluted with chloroform and washed with water. The chloroform extract was dried ($MgSO_4$) and evaporated to dryness. The residue was reduced with sodium borohydride and deblocked with sodium in liquid ammonia as in (ii) above to give O-α-D-glucopyranosyl-(1→4)-garamine (15 mg.) which was identical with that prepared in (i) above.

iv. 5,2′,4′-Tri-O-acetyl-1,3,3′-tri-N-carbobenzoxygaramine (800 mg.), 2-O-benzyl-3,4,6-tri-O-p-nitrobenzoyl-α-D-glucobromide (871 mg.) mercuric cyanide (406 mg.) and anhydrous calcium sulphate (4.2 g.) in dry toluene (75 ml.) were stirred and heated under nitrogen at 70° for 2 days. The mixture was cooled, filtered and the residue was washed with ethyl acetate (200 ml.). The combined filtrate and washing, was washed twice with 20% potassium bromide solution (300 ml.) and then with water (300 ml.) and dried ($MgSO_4$). The solvent was evaporated and the residue was chromatographed on fifteen 8 × 16 inches, 2 mm. thick silica gel PF plates using benzene-ether:methanol:49.5:49.5:1 as the eluent, to give O-[2-O-benzyl-3,4,6-tri-O-nitrobenzoyl-α-D-glucopyranosyl-(1→4)]-5,2′,4′-tri-O-acetyl-1,3,3′-tri-N-carbobenzoxy-garamine (375 mg.), (Found: C, 60.07; H, 5.00; N, 5.68. $C_{77}H_{76}N_6O_{29}$ requires: C, 59.36; H, 4.92; N, 5.40%), δ($CDCl_3$) ↑1.28, 1.42 (3H, broad s, 4″—$CH_3$), 1.95, 1.98, 2.05 (9H, broad s, OAc), 2.90 (3H, broad s, 3″—$NCH_3$), 7.20 (5H, broad s, $C_6H_5CH_3$—O—), 7.35 (15H, broad s, $C_6\underline{H}_5$—$CH_3OCO$), and 8.17 ppm. (12H, broad s, p-$NO_2$-benzoate).

The trisaccharide (320) mg. was dissolved in a mixture of methanol (180 ml.) and concentrated ammonium hydroxide (20 ml.) and the solution was stirred at 25° for 18 hours. The solution was evaporated and the residue was taken up in liquid ammonia (100 ml.) and cooled in a dry-ice acetone bath. Sodium (400 mg.) was added and the mixture was stirred for two hours. Excess sodium was destroyed by careful addition of water (10 ml.) and the solution was allowed to warm up gradually to 25°. The residue was placed on a column (30 ml.) of Biorex 7C (H+ form) resin, washed with distilled water (30 ml.) to remove neutral impurities, and the product eluted with 1.5M ammonium hydroxide. The eluate was evaporated to dryness and the residue was chromatographed on a silica gel (5 g.) column using the lower phase of a chloroform-methanol-ammonium hydroxide solution (1:1:1) as the eluent, to give O-α-D-glucopyranosyl-(1→4)-garamine (34 mg.) as a colorless solid after passage down Amberlite IR401S resin and lyophilization. It was identical in all respects with the product described in (i) above.

EXAMPLE 30

3,4-Di-O-acetyl-6-azido-1,2,6-trideoxy-D-arabinohex-1-enopyranose 3,4-Di-O-acetyl-1,2-dideoxy-6-O-tosyl-D-arabinohex-1-enopyranose (50g.) was dissolved in hexamethylphosphoramide (800 ml.) and sodium azide (34 g.) was added and the solution was stirred at 25° for 24 hours. The hexamethylphosphoramide was distilled off under high vacuum and the residue was taken up in chloroform and washed with water. The chloroform extract was dried ($MgSO_4$), filtered and evaporated to give a crude gum which was chromatographed on a silica gel column (150 × 7.5 cm.) using 7% acetone in hexane as the eluent to give 3,4-di-O-acetyl-6-azido-1,2,6-trideoxy-D-arabinohex-1-enopyranose (25 g.) as a colorless gum, (Found: C, 47.23; H, 5.30; N, 16.37. $C_{10}N_{13}N_3O_5$ requires: C, 47.06; H, 5.13; N, 16.46%), $[\alpha]_D^{26}$ × 25.1° ($CH_3OH$), νmax ($CHCl_3$) 2110, 1755, 1660, 1220, 1040 cm. $^{-1}$, δ($CDCl_3$) 2.06, 2.09 (6H, s, OAc), 4.91 (1H, ddd, J = 6.5Hz, 3.0Hz, 1Hz, $H_2$), and 6.53 ppm. (1H, dd, J = 6.5Hz, 1.5Hz, $H_1$).

EXAMPLE 31

3,4-Di-O-acetyl-6-azido-2,6-dideoxy-2-nitroso-α-D-glucopyranosyl chloride 3,4-Di-O-acetyl-6-azide-1,2,6-trideoxy-D-arabinohex-1-enopyranose (4.5g.) was dissolved in dry ether and an excess of nitrosyl chloride was added to the solution at −30°. The mixture was allowed to stand at −30°for 1 hour and fifteen minutes. The solution was evaporated to dryness and the residue was crystallized from dry ether to give 3,4-di-O-acetyl-6-azido-2,6-dideoxy-2-nitroso-α-D-glucopyranosyl chloride (4.55 g.) as colorless needles, m.p. 190° -111° , (Found: C, 37.39; H, 3.94; N, 17.42; Cl, 11.12. $C_{10}H_{13}N_4O_6Cl$ requires: C, 37.45; H, 4.08; N, 17.47; Cl, 11.06% ). $[\alpha]_D^{26}$ + 248.8° ($CHCl_3$), νmax ($CHCl_3$) 2100, 1760, 1220, 1050 cm. $^{-1}$, δ($CDCl_3$) 2.00, 2.07 (6H, s, OAc), and 6.70 ppm. (1H, d, J = 3.7Hz, $H_1$).

EXAMPLE 32

Antibiotic JI-20A 5,2',4'-Tri-O-acetyl-1,3,3'-tri-N-carbobenzoxygaramine (6g.) and 3,4-di-O-acetyl-2,6-azido-2,6-azido-2,6-dideoxy-2-nitroso-α-D-glucopyranosyl chloride (4.5g.) were dissolved in dry, redistilled dimethylformamide (205 ml.) and the solution was allowed to stand at 25° for 94 hours. The reaction mixture was poured into ice-water and the precipitate was filtered, dried and chromatographed on a silica gel column (160 × 2.5 cm.) using 1% methanol in chloroform as the eluent, to give O-[3,4-di-O-acetyl-6-azido-2,6dideoxy-2-oximino-α-D-glucopyranosyl-(1→4)]-5,2',4'tri-O-acetyl-1,3,3'-tri-N-carbobenzoxygaramine (2.4 g.) as a colorless amorphous solid, m.p. 129°–137°, (Found: C, 55.77; H, 5.59; N, 8.47. $C_{53}H_{63}N_7O_{21}$ requires: C, 56.13; H, 5.60; N, 8.65%), $[\alpha]_D^{26}$ + 112.0° ($CH_3OH$), νmax ($CHCl_3$) 3350, 2110, 1740, 1710, 1220, 1035 cm.$^{-1}$, δ($CDCl_3$) † 1.23, 1.36 (3H, broad s, 4''—$CH_3$), 1.92 (15H, broad s, OAc), 2.82 (3H, broad s, 3''—$NCH_3$), 5.02 (6H, broad s, —$CH_2C_6H_5$), 6.12 (1H, broad s, $H_{1'}$), and 7.23 ppm. (15H, broad s, —$CH_2C_6\underline{H}_5$). O, [3,4-Di-O-acetyl-6-azido-2,6-dideoxy-2-oximino-αD-glucopyranosyl-(1→4)]-5,2',4'-trio-O-acetyl-1,3,3'-tri-N-carbobenzoxygamine (1.3 g.) and acetic anhydride (2 ml.) were dissolved in dry pyridine (10 ml.) and the solution was allowed to remain at 25° for eighteen hours. The reaction mixture was poured into water and the solid O-[2,3,4-tri-O-acetyl-6-azido-2,6-dideoxy-2-oximino-α-D-glucopyranosyl-(1→4)]-5,2', 4'-tri-O-acetyl-1,3,3'-tri-N-carbobenzoxygaramine was filtered off and dried.

The acetate was dissolved in tetrahydrofuran (45 ml.) and cooled to 0°. A 1M solution of diborane in tetrahydrofuran (18 ml.) was added dropwise and the mixture was kept at 7° for 18 hours. Excess reagent was destroyed by dropwise addition of water until no further effervescence occurred. The solution was evaporated to dryness and the residue was taken up in methanol and hydrogenated over 30% palladium on carbon at 60 p.s.i. at 25° for 18 hours. The catalyst was filtered off and the filtrate was evaporated to dryness to give an amorphous solid. The latter was dissolved in aqueous dioxan (1:1) (60 ml.) containing sodium hydroxide (3 g.) and the solution was heated under reflux at 120° for 16 hours. The solution was neutralized with Amberlite IRC 50 resin and the slurry was poured onto a column. The resin was washed with water and the Antibiotic JI-20A was then eluted with 1.5M ammonium hydroxide. The basic eluate was evaporated to dryness and chromatographed on a silica gel column (110 × 2.5 cm.) using chloroform-methanol-7 % ammonium hydroxide (2:1:1) as the eluent to give Antibiotic JI-20A which after passage down Amberlite IR401S resin and lyophilization was obtained as a colorless amorphous solid (34 mg.), m.p. 158°–168°, (Found: C, 45.44; H, 7.73; N, 13.14. $C_{19}H_{39}N_5O_9.CO_2$ requires: C, 45.70; H, 7.48; N, 13.33%), m/e 482 ($M^+$+ 1), $[\alpha]_D^{26}$ × 149.8° ($H_2O$), νmax (KCl), 3350, 1050 cm.$^{-1}$, δ($D_2O$) 1.16 (3H, s, 4''—$CH_3$), 2.48 (3H, s, 3''—$NCH_3$), 5.02 (1H, d, J = 4Hz, $H_{1''}$), and 5.26 ppm. (1H, d, J = 3.5Hz, $H_{1'}$), [θ]290 - 11,000 (TACu), [θ]290 - 8,840 (Cupra A).

EXAMPLE 33

Gentamicin B

O-[3,4-Di-O-acetyl-6azido-2,6-dideoxy-2-oximino-α-D-glucopyranosyl- (1→4)]-5,2',4'tri-O-acetyl-1,3,3'-tri-N-carbobenzoxygaramine (500 mg.) in glacial acetic acid (7 ml.) was treated with levulinic acid (1 g.) and 1N hydrochloric acid (1 ml.) and the mixture was stirred at 25° for 18 hours. The mixture was taken up in methylene chloride and the latter was washed with aqueous sodium bicarbonate, water, dried ($MgSO_4$) and evaporated to dryness. The resulting solid was dissolved in dioxan (10 ml.) containing water (1 ml.) and cooled at 5°. Sodium borohydrate (100 mg.) in dioxan (2 ml.) and water (4 ml.) was added dropwise with stirring. Stirring was maintained at 5° for one half hour and at 25° for 1 hour. The reaction was quenched with acetic acid and evaporated to dryness. The resulting solid was taken up in methanol (40 ml.) and hydrogentated over 10% palladium on carbon at 60 p.s.i. at 25° for 19 hours. The catalyst was filtered off and the filtrate was evaporated to dryness and then taken up in methanol-concentrated ammonium hydroxide (1:2) (40 ml.) and heated in a bomb at 100° for 16 hours. The solution was evaporated and the resulting glass was heated under reflux for 16 hours with 5% aqueous sodium hydroxide (30 ml.). The mixture was cooled and neutralized with Amberlite IRC50 resin and the slurry was poured onto a column. The residue was washed with water and the antibiotic was then eluted with 1.5 M ammonium hydroxide (1 liter). The basic eluate was evaporated to dryness and chromatographed on a silica gel column (110 × 2.5 cm) using the lower phase of a chloroform-methanol-ammonium hydroxide solution (1:1:1) as the eluent to give gentamicin B (40 mg.) as a colorless amorphous solid after passage down Amberlite IR401S resin followed by lyophilization, m.p. 157°–159° (ethanol solvate), (Found: C, 47.78; H, 8.38; N, 10.59, $C_{19}H_{38}N_{10}.C_2H_5OH$ requires: C, 47.70; H, 8.41; N, 10.60%), m/e 483.26665 ($M^+$+1, $C_{19}H_{39}N_4O_{10}$ requires m/e 483.26661), $[\alpha]_D^{26}$ + 175.2° ($H_2O$), νmax (KCl) 3300, 1050 cm$^{-1}$, δ($D_2O$) 1.22 (3H, s, 4''-$CH_3$), 1.23 (1H, q, J = 12Hz, $H_{2\alpha}$), 1.98 (1H, dt, J = 3.75 Hz, J = 12.5Hz, $H_{2eg}$), 2.52 (3H, s, 3''-$NCH_3$), 4.04 (1H, d, J = 12.5Hz, $H_{5''}$eg), 5.07 (1H, d, J = 4Hz, $H_{1''}$) and 5.31 ppm (1H, d, J = 3.5 Hz $H_{1'}$), [θ]290 - 6,830 (TACu).

EXAMPLE 34

4-O-Acetyl-3-deoxy-6-O-tosyl-D-glucal

3Deoxy-D-signal (2 g.) was dissolved in dry pyridine (50 ml.) and the solution was cooled in an ice bath. Tosyl chloride (8.8 g.) in dry pyridine (100 ml.) at 0° was added and the mixture was maintained at 7° for 22 hours. Acetic anhydride (10 ml.) was then added and the mixture was allowed to remain at 7° for 19 hours. The mixture was concentrated to small volume, poured into water and extracted with chloroform. The chloroform extract was washed with water, dried ($MgSO_4$) and evaporated to dryness. The residue was azeotroped with toluene and then chromatographed on a silica gel column (160 × 2.5 cm.) using chloroform as the eluent to give 4-O-acetyl-3-deoxy-6-O-tosyl-D-glucal (3.83 g.) as colorless plates from chloroform, m.p. 76°–79°, (Found: C, 54.99; H, 5.81; S, 10.02. $C_{15}H_{18}O_6S$ requires: C, 55.20; H, 5.56; S, 9.83%), m/e 327 ($M^+$+1), $[\alpha]_D^{26}$ + 105.5° ($CH_3OH$) ν max (film) 1740, 1660, 1360, 1240 cm.$^{-1}$, δ($CDCl_3$) 2.01 (3H, s, OAc), 2.43 (3H, s, $\underline{CH_3}$ $C_6H_4SO_2O$-), 4.66 (1H, ddd, J = 6Hz, J = 4.5Hz, J = 3Hz, $H_2$) and 6.25 ppm (1H, ddd, J = 6Hz, J = 2Hz, J = 2Hz, $H_1$).

EXAMPLE 35

4-O-Acetyl-2,3-dideoxy-2-nitroso-6O-tosyl-α-D-glucopyranosyl chloride

4-O-Acetyl-3-deoxy-6-O-toxyl-D-glucal (0.79 g.) was dissolved in dry ethyl acetate (50 ml.) and the solution was cooled in an ice bath. A solution of nitrosyl chloride in dry ethyl acetate (0.25 M) (9.7 ml.) was added and the mixture was stirred at 0° for 90 minutes. The green solution was evaporated in vacuo and the residual gum was triturated with dry ether and dried to give the 4-O-acetyl-2,3-dideoxy-2-nitroso-6O-tosyl-α-D-glucopyranosyl chloride (0.7 g.) as a colorless fluff, (Found: C, 46.21; H, 4.78; N, 3.24; Cl, 8.02; S, 7.83. $C_{15}H_{18}NO\text{-}CLS$ requires: C, 45.96; H, 4.63; N, 3.57; Cl, 9.05; S, 8.18%), $[\alpha]_D^{26}$ + 85.3° ($CHCl_3$), $\nu$max ($CHCl_3$) 1740, 1360, 1220, 1040 cm$^{-1}$, $\delta(CDCl_3)$ 2.02, 2.09 (3H, s, OAc), 2.45 (3H, s, C$\underline{H_3}$ $C_6H_4SO_2O$), 6.53 and 6.65 ppm (1H, d, J = 3.5 Hz, $H_1$).

EXAMPLE 36

O-[4-O-Acetyl-2,3-dideoxy-2-oximino-6O-tosyl-α-D-glucopyranosyl-(1→4)]-5,2', 4'-tri-O-acetyl-1,3,3'-tri-N-carbobenzoxygaramine 5,2',4'-Tri-O-acetyl-1,3,3'-tri-N-carbobenzoxygaramine (25.5 g.) and 4-O-acetyl-2,3-dideoxy-2-nitroso-6-O-tosyl-α-D-glucopyranosyl chloride (23.5 g.) were dissolved in dry redistilled dimethylformamide (650 ml.) and the solution was allowed to remain at 25° for 91 hours. The reaction mixture was poured into ice-water and the precipitate was filtered, dried and chromatographed on a silica gel column (160 × 7.5 cm) using 0.5% methanol in chloroform as the eluent, to give O-[4-O-acetyl-2,3-dideoxy-2-oximino-6-O-tosyl-α-D-glucopyranosyl-(1→4)][-5,2',4'-tri-O-acetyl-1,3,3'-tri-N-carbobenzoxygaramine (18 g.) as a colorless amorphous solid, m.p. 123°–132°, (Found: C, 57.70; H, 5.77; N, 4.64; S, 2.46. $C_{58}H_{68}N_4O_{22}S$ requires: C, 57.80; H, 5.69; N, 4.65; S, 2.66%), $[\alpha]_D^{26}$+ 116.2° ($CH_3OH$), $\nu$max ($CHCl_3$) 3330, 1740, 1710, 1360, 1220, 1030 cm.$^{-1}$, $\delta(CDCl_3)$ †1.23, 1.37 (3H, broad s, 4"—$CH_3$), 1.88, 1.90, 1.99 (12H, broad s, OAc), 2.38 (3H, broad s, $CH_3C_6H_4SO_2O$—) 2.84 (3H, broad s, 3"—$NCH_3$), 5.02 (6H, broad m, $C_6H_5C\underline{H_2}OCO$—), and 7.26 ppm (15H, broad s. $C_6H_5CH_2OC\underline{O}$-).

EXAMPLE 37

O-2,6-Diamino-2,3,6-trideoxy-α-D-glucopyranosyl-(1→4)-garamine (3'-deoxyantibiotic JI-20A)

O-2,6-Diamino-2,3,6-trideoxy-α-D-glucopyranosyl-(1→4)-garamine

O-[4-O-Acetyl-2,3-dideoxy-2-oximino-6-O-tosyl-α-D-glucopyranosyl-(1→4)]-5,2', 4'-tri-O-acetyl-1,3,3'-tri-N-carbobenzoxygaramine (5 g.) and sodium azide (5.7 g.) were dissolved in hexamethylphosphoramide (180 ml.) and the solution was stirred at 25° for 65 hours. The reaction mixture was poured into water and extracted with ether and the latter extract was dried ($MgSO_4$) and evaporated to give the O-[4-O-acetyl-6-azido-2,3-trideoxy-2-oximino-α-D-glucopyranosyl-(1→4)]-5,2',4'-tri-O-acetyl-1,3,3'-tri-N-carbobenzoxygaramine as a colorless amorphous solid.

The crude azide was dissolved in dry pyridine (25 ml.) and acetic anhydride (5 ml.) was added and the mixture was allowed to remain at 25° for 19 hours. The reaction mixture was poured into water and the solid O-[2,4-di-O-acetyl-6-azido-2,3,6-trideoxy-2-oximino-α-D-glucopyranosyl-(1→4)]-5,2',4'-tri-O-acetyl-1,3,3'-tri-N-carbobenzoxygaramine was taken up in chloroform, dried ($MgSO_4$) an evaporated.

The acetate was dissolved in dry tetrahydrofuran (100 ml. and cooled to 0°. A 1M solution of diborane in tetrahydrofuran (41.5 ml.) was added dropwise and the mixture was allowed to remain at 7° for 30 hours. Excess reagent was destroyed by dropwise addition of water. The solution was evaporated to dryness and the residue was taken up in methanol and hydrogenated over 10% palladium on carbon at 60 p.s.i. at 25° for 19 hours. The catalyst was filtered off and the filtrate was evaporated to dryness and then taken up in methanol-concentrated ammonium hydroxide (1:2) (60ml.) and heated in a bomb at 100° for 16 hours. The solution was evaporated and the resulting glass was heated under reflux for 16 hours with 5% aqueous sodium hydroxide (60 ml.). The mixture was cooled and neutralized with Amberlite IRC50 resin and the slurry was poured onto a column. The resin was washed with water and the antibiotic was then eluted with 1.5M ammonium hydroxide (2 liters). The basic eluate was evaporated to dryness and chromatographed first on a silica gel column (160 × 5 cm.) using chloroform-methanol-7% ammonium hydroxide as the eluent and then on a silica gel column (100 × 1 cm.) using the lower phase of a chloroform-methanol-ammonium hydroxide (1:1:1) system as the eluent to give after passage down Amberlite IRA401S resin and lyophylization, O-2,6-diamino-2,3,6-trideoxy-α-D-gluco pyransoyl-(1→4)-garamine (69 mg.) as a colorless solid, m.p. 130° (softens at 52° ), (Found: C, 47.85; H, 8.17; N. 13.48. $C_{19}H_{39}N_5O_8 \cdot CO_2$ requires: C, 47.14; H, 7.71; N, 13.75%), m/e 466 (M++1), $[\alpha]_D^{26}$+ 158.4° ($H_2O$), $\nu$max (KCl) 3280, 1050, 1020 cm.$^{-1}$, $\delta(D_2O)$ 1.14 (3H, s, 4"—$CH_3$), 2.45 (3H, s, 3"—$NCH_3$), 2.48 (1H, dd, J = 10.5 Hz, $H_{3''}$), 3.23 (1H, d, J = 12Hz, $H_{5e''}$), 3.71 (1H, d, J = 10.5 Hz, J = 4Hz, $H_{2''}$), 3.97 (1H, d, J = 12Hz, $H_{53''}$), 5.01 (1H, d, J = 4Hz, $H_{1''}$) and 5.07 ppm (1H, d, J = 3.5Hz, $H_{1'}$), [θ]285 -7,970 (TACu), [θ]285 - 6,480 (Cupra A):

EXAMPLE 38

4-O-Acetyl-6-azido-3,6-dideoxy-D-glucal

4-O-Acetyl-3-deoxy-6-O-tosyl-D-glucal (550 mg.) and sodium azide (550 mg.) were dissolved in hexamethylphosphoramide (50 ml.) and the mixture was stirred at 25° for 24 hours. The reaction mixture was poured into ether and extracted with water and the ether extract was dried ($MgSO_4$) and evaporated and the product was chromatographed on a silica gel column (58 × 2.5 cm) using 7% acetone in hexane as the eluent to give 4-O-acetyl-6-azido-3,6-dideoxy-D-glucal (200 mg.) as a colorless oil, (Found: C, 48.84; H, 5.33; N,21.49. $C_8H_{11}N_3O_3$ requires: C, 48.72; H, 5.62; N, 21.31%), $[\alpha]_D^{26}$ = 158.8° ($CH_3OH$), $\nu$max (film) 2100, 1720, 1660, 1220, 1050 cm.$^{-1}$, $\delta($ $CDCl_3$) 2.09 (3H, s, OAc), 4.72 (1H, ddd, H = 6Hz, J = 4.5Hz, J = 3Hz, $H_2$) and 6.39 ppm (1H, ddd, J = 2Hz, J = $H_1$. )

EXAMPLE 39

4-O-Acetyl-6-azido-2,3,6-trideoxy-2-nitorso-α-D-glucopyranosyl chloride

4-O-Acetyl-6-azido-3,6-dideoxy-D-glucal (112 mg.) was dissolved in dry ethyl acetate (15 ml.) and the solution was cooled to 0°. A solution of nitrosyl chloride (55 mg/0.53 ml) in dry ethyl acetate was added and the mixture was stirred for thirty minutes. The mixture was evaporated to dryness, triturated with dry ether and dried in vacuo to give 4-O-acetyl-6-azido-2,3,6-trideoxy-2-nitroso-α-D-glucopyranosyl chloride (146 mg.) as a colorless gum, (Found: C, 36.74; H, 4.32; N, 19.89; Cl, 12.53. $C_8H_{11}N_4O_4Cl$ requires: C, 36.58; H, 4.22; N, 21.33; Cl, 13.50%), $[\alpha]_D^{26}+$ 98.8° ($CHCl_3$), $\nu$max ($CHCl_3$), 2110, 1750, 1220, 1040 cm.$^{-1}$, $\delta(CDCl_3)$ 2.09, 2.11 (3H, s, OAc) and 6.71, 6.84 ppm (1H, d, J = 3.5Hz, $H_1$) (3:2).

EXAMPLE 40

O-2,6-Diamino-2,3,6-trideoxy-α-D-glucopyranoayl-(1→4)-garamine (3'-deoxyantibiotic JI-20A)

5,2',4'-Tri-O-acetyl-1,3,3'-tri-N-carbobenzoxygaramine (7.1 g.) and 4-O-acetyl-6-azido-2,3,6-trideoxy-2-nitroso-α-D-glucopyranosyl chloride (4.2 g.) were dissolved in dry redistilled dimethylformamide (160 ml.) containing N,N,2,6-tetramethylaniline (0.9 g.) and the solution was allowed to stand at 25° for 94 hours. The solution was concentrated and poured into icewater and the precipitate was filtered, dried and chromatographed on a silica gel column (150 × 5 cm.) using 1% methanol in chloroform as the eluent to give O-[4-O-acetyl-6-azido-2,3,6-trideoxy-2-oximino-α-D-glucopyranosyl-(1→4)]-5,2',4'-tri-O-acetyl-1,3,3'-tri-N-carbobenzoxygaramine (6.3 g.) as a colorless amorphous solid, m.p. 125°-133°, (Found: C, 57.90; H, 5.82; N, 8.65. $C_{51}H_{61}N_7O_{19}$ requires: C, 56.92; H, 5.71; N, 9.11%), $[\alpha]_D^{26} + $ 150.5° ($CH_3OH$), $\nu$max ($CHCl_3$) 3340, 2110, 1740, 1700, 1220, 1030 cm.$^{-1}$, $\delta$ ($CDCl_3$) † 1.27, 1.38 (3H, broad s, 4''-$CH_3$), 1.91, 2.01 (12H, broad s, OAc), 2.86 (3H, broad s, 3''-$NCH_3$), 5.04, 5.11. 5.17 (6H, broad s, —$CH_2C_6H_5$) and 7.30, 7.31 ppm (15H, s, —$CH_2C_6H_5$). The azide was reacted as before to give O-2,6-diamino-2,3,6-trideoxy-α-D-glucopyranosyl-(1→4)]-garamine.

EXAMPLE 41

3'-Deoxygentamicin B

O-[4-O-Acetyl-2,3-dideoxy-2-oximino-6-O-tosyl-α-D-glucopyranosyl-(1→4)]-5,2',4'-tri-O-acetyl-1,3,3'-tri-n-carbobenzoxygaramine (3 g.) was dissolved in glacial acetic acid (75 ml.). Levulinic acid (7.5 ml.) and 1N hydrochloric acid (10 ml.) were added and the mixture was allowed to remain at 25° for 20 hours. The reaction mixture was diluted with methylene chloride (700 ml.) and extracted with three portions of 5% aqueous sodium bicarbonate and then washed with water. The solvent was evaporated and the residue was taken up in dioxan (100 ml.) and water (10 ml.) and the solution was cooled to 5°. Sodium borohydride (2 g.) in dioxan (20 ml.) and water (40 ml.) was added dropwise with stirring at 5° and the stirring continued for 0.5 hours at 5° and 1 hour at 25°. The excess sodium borohydride was destroyed by dropwise addition of acetic acid and the resulting solution was evaporated to dryness to give O-[4-O-acetyl-3-deoxy-6-O-tosyl-α-D-glucopyranosyl-(1→4)]-5,2',4'-tri-O-acetyl-1,3,3'-tri-N-carbobenzoxygaramine.

1. A portion of the latter (150 mg.) was taken up in methanol saturated with ammonia at 0° (40 ml.) and heated in a bomb at 100° for 16 hours. The solution was evaporated to dryness and the residue was taken up in 5% aqueous sodium hydroxide (50 ml.) and heated under reflux for sixteen hours. The reaction mixture was neutralized with Amberlite IRC50 resin and the resin was transferred to a column and washed with water (1 liter). The antibiotic was then eluted with 1.5 N ammonium hydroxide (1.5 liter) and the latter was evaporated to dryness and chromatographed on a silica gel column (160 × 2.5 cm) using chloroform-methanol-ammonium hydroxide (7%) (1:2:1) as the eluent, and then rechromatographed on a silica gel column (110 × 2.5 cm.) using the lower phase of a chloroform-methanol-ammonium hydroxide system (1:1:1) as the eluent to give 3'-deoxygentamicin B as a colorless solid (9 mg.) after passage down Amberlite IR401S and lyophilization, m/e 467 ($M^+$+1) (Calculated for $C_{19}H_{38}N_4O_9$: $M^+$+1, 467), $\delta(D_{20} + DCl)$ 1.30 (3H, s, 4''-$CH_3$), 2.89 (3H, s, 3''-$NCH_3$), 5.08 (1H, d, $J_1''$, 2'' = 3.15Hz, $H_1''$) and 5.41 ppm (1H, d, $J_1'$, 2' = 4Hz, $H_1'$).

ii. O-[4-O-Acetyl-3-deoxy-6-O-tosyl-α-D-glucopyranosyl-(1→4)]-5,2',4'-tri-O-acetyl-1,3,3'-tri-N-carbobenzoxygaramine (2.5 g.) was dissolved in dry pyridine (25 ml.) and acetic anhydride (2.3 ml.) was added and the mixture was allowed to remain at 25° for 18 hours. The reaction mixture was poured into water and the precipitate was filtered off and dried to give the acetate (2.5 g.). The acetate (2.5 g.) and sodium azide (2.8 g.) were dissolved in hexamethylphosphoramide (90 ml.) and the solution was stirred at 25° for 65 hours. The reaction mixture was poured into water and extracted with ether and the latter extract was dried ($MgSO_4$) and evaporated to give the azide as a colorless amorphous solid. The azide was taken up in methanol and hydrogenated over 10% palladium on carbon at 60 p.s.i. at 25° for 19 hours. The catalyst was filtered off and the filtrate was evaporated to dryness. The resulting glass was heated under reflux for 16 hours with 5% aqueous sodium hydroxide (100 ml.). The mixture was cooled and neutralized with Amberlite IRC50 resin and worked up as in (i) to give 3'-deoxygentamicin B which was identical with that prepared in (i) above.

EXAMPLE 42

3'-Deoxy-6'-N-methylgentamicin B

O-[3-deoxy-2,4-di-O-acetyl-6-O-tosyl-α-D-glucopyranosyl-(1→4)]-5,2',4'-tri-O-acetyl-1,3,3'-tri-N-carbobenzoxygaramine (230 g.) was dissolved in a saturated solution of methylamine in methanol (60 ml.) at 0° and the mixture was heated in a bomb at 130° for 17 hours. The solution was evaporated to dryness and the residue was taken up in 5% aqueous sodium hydroxide (45 ml.) and the solution was heated under reflux for 16 hours. The reaction mixture was neutralized with Amberlite IRC 50 resin and the resin was transferred to a column and washed with water (1 liter). The antibiotic was then eluted with 1.5N ammonium hydroxide (1.5 l.) and the latter was evaporated to dryness and chromatographed on a silica gel column (145 × 2.5 cm.) using chloroform-methanol-7% ammonium hydroxide (1:2:1) as the eluent to 3'-deoxy-6'-N-methylgentamicin B as a colorless solid (32 mg.) after passage down Amberlite IR401S resin and lyophilization, m/e 481 ($M^+$+1), $\delta$ ($D_2O$), 1.13 (3H, S, 4''—$CH_3$), 2.25 (3H, S, 6'—$NCH_3$), 2.44 (3H, S, 3''—$NCH_3$), 5.00 (1H, d, J=3.5 Hz, $H_1''$) and 5.08 ppm. (1H, d, J=3.5 Hz, $H_1''$) and 5.08 ppm. (1H, d, J=3.5 Hz, $H_1'$).

EXAMPLE 43

1,3,2',3''-Tetra-N-carbobenzoxy-3'-deoxygentamicin $X_2$ 1,3,2',3''-Tetra-N-carbobenzoxy-3'-deoxygentamicin $X_2$ 3'-Deoxygentamicin $X_2$ (900 mg.) was dissolved in water (25 ml.) containing sodium carbonate (0.5 g.) and carbobenzoxy chloride (4 ml.) was added. The mixture was stirred at 25° for 18 hours. The insoluble material was filtered off, dried and chromatographed on a silica gel column (110 × 2.5 cm.) using 9% methanol in chloroform as the eluent. 1,3,2',3''-Tetra-N-carbobenzoxy-3'-deoxygentamicin $X_2$ was obtained as a colorless amorphous solid (1.06 g.), (Found: C, 60.90; H, 6.36; N, 5.70. $C_{51}H_{62}N_4O_{17}$ requires: C, 61.07; H, 6.23; N, 5.59%), $[\alpha]_D^{26}$ + 76.5° (DMSO), $\nu$max (CHCl$_3$) 3300, 1690, 1540, 1035 cm.$^{-1}$, $\delta$(d$_6$-DMSO) † 0.90 (3H, broad s, 4'''—CH$_3$), 2.98 (3H, broad s, 3''-NCH$_3$), 5.02 (8H, broad s, C$_6$H$_5$CH$_2$OCO) and 7.32 ppm (2OH, broad s, C$_6$H$_5$CH$_2$O$\overline{\text{C}}$O).

EXAMPLE 44

4',2''-Di-O-acetyl-1,3,2',3''-tetra-N-carbobenzoxy-3'-deoxy-6'-O-tritylgentamicin $X_2$.

1,3,2',3''-Tetra-N-carbobenzoxy-3'-deoxygentamicin $X_2$ (0.99 g.) and trityl chloride (0.293 g.) were dissolved in dry pyridine (10 ml.) and the reaction was allowed to remain at 25°. After 24 hours additional trityl chloride (0.114 g.) was added. After 46 hours, the reaction mixture was poured into ice-water and the trityl derivative was filtered off and dried (1.22 g.). The latter was taken up in dry pyridine and acetic anhydride (4 ml.) was added. After 18 hours at 25° the solution was poured into ice-water and the precipitate was collected. Chromatography on a silica gel column (110 × 2.5 cm.) using 2% methanol in chloroform as the eluent gave 4',2''-di-O-acetyl-1,3,2',3''-tetra-N-carbobenzoxy-3'-deoxy-6'-O-tritylgentamicin $X_2$ as a colorless amorphous solid (0.9 g.).

EXAMPLE 45

4',2''-Di-O-acetyl-1,3,2',3''-tetra-N-carbobenzoxy-3'-deoxy-6'-O-tosylgentamicin $X_2$ 4',2''-Di-O-acetyl-1,3,2',3''-tetra-N-carbobenzoxy-3'-deoxy-6'-O-tritylgentamicin $X_2$ (0.9 g.) was dissolved in glacial acetic acid (35 ml.) and the solution was heated on a steam bath for 3 hours. The mixture was evaporated to dryness and the residue was taken up in chloroform, washed with water, dried (MgSO$_4$) and evaporated to give 4',2''-di-O-acetyl-1,3,2',3''-tetra-N-carbobenzoxy-3'-deoxygentamicin $X_2$ as a colorless amorphous solid (0.61 g.). The latter was dissolved in pyridine (10 ml.) and tosyl chloride (0.6 g.) was added. The reaction mixture was allowed to stand at 25° for 23 hours. The reaction mixture was poured into ice-water, extracted with chloroform and the latter was washed with water, dried (MgSO$_4$) and evaporated to give a gum. The crude product was chromatographed on a silica gel column (110 × 2.5 cm.) and eluted with 3.5% methanol in chloroform to give 4',2''-di-O-acetyl-1,3,2',3''-tetra-N-carbobenzoxy-3'-deoxy-6'-O-tosylgentamicin $X_2$ as a colorless amorphous solid (163 mg.), (Found: C, 59.87; H, 5.87; N, 4.26; S, 2.75. $C_{62}H_{72}N_4O_{21}S$ requires: C, 59.99; H, 5.85; N, 4.51; S, 2.58%), $\nu$max (CHCl$_3$) 3400, 3300, 1725, 1500, 1220, 1030 cm.$^{-1}$, $\delta$(CDCl$_3$) † 0.99 (3H, broad s, 4''-CH$_3$), 1.83 (6H, broad s, 4',2''-OAc), 2.41 (3H, broad s, CH$_3$C$_6$H$_4$SO$_2$O-), 2.88 (3H, broad s, 3''—NCH$_3$), 5.02 (8H, broad m, C$_6$H$_5$CH$_2$OCO) and 7.27, 7.31, 7.69, 7.82 ppm (24H, broad s, aromatic H).

EXAMPLE 46

O-2-Amino-6-methylamino-2,3,6-trideoxy-α-D-glucopyranosyl-(1→4)-garamine (3'-deoxy-6'-N-methylantibiotic JI-20A).

4',2''-Di-O-acetyl-1,3,2',3''-tetra-N-carbobenzoxy-3'-deoxy-6'-O-tosylgentamicin $X_2$ (144 mg.) was dissolved in dry methanol (2 ml.) and saturated with methylamine at 0°. The solution was heated at 135° in a sealed bomb for 18 hours. The solution was cooled and evaporated to dryness. The residue was heated under reflux with 5% aqueous sodium hydroxide (3 ml.) for 18 hours. The solution was neutralized with Amberlite IRC50 resin and the slurry was transferred to a column and washed with water. The crude antibiotic was eluted from the resin with 1.5N ammonium hydroxide and the solution was evaporated to dryness. The residue was heated under reflux with hydrazine hydrate (1 ml.) at 125° for 24 hours, and then evaporated to dryness. The residue was chromatographed on a silica gel column (110 × 1 cm.) using the lower phase of a chloroform-methanol-concentrated ammonium hydroxide system (1:1:1) as the eluent. The relevant fractions were combined, passed over Amberlite IRA 401S (OH$^-$) resin and lyophilized to give O-2-amino-6-methylamino-2,3,6-trideoxy-α-D-glucopyranosyl-(1→4)-garamine (20 mg.) as a colorless amorphous solid, m/e 480 (M$^+$+1) ($C_{20}H_{41}O_8N_5$ requires: M$^+$ +1 at m/e 480). barium oxide (1.05 g.) and barium hydroxide (1.25 g.) were added. The mixture was stirred and cooled to −10° and benzyl bromide (0.75 ml.) was added dropwise. The mixture was allowed to warm up to room temperature and after 24 hours the solution was diluted with chloroform and filtered. The filtrate was evaporated to dryness and the resulting gum solidified on trituration with water. Chromatography on silica gel plates using 7% methanol in chloroform as the eluent gave 2'-O-benzyl-1,3-di-N-carbobenzoxy-4,5-O-isopropylidene-garamine-3',4'-oxazolidinone (0.26 g.) as a colorless amorphous solid, (Found: C, 63.18; H, 6.28; N, 5.97. $C_{40}H_{47}N_3O_{11}$ requires: C, 64.40; H, 6.31; N, 5.64%), $[\alpha]_D^{26}$ + 63.8° (C$_2$H$_5$OH), $\lambda$ max (CH$_3$OH) 208 m$\mu$ ($\epsilon$23,800), $\nu$ max (CHCl$_3$) 3400, 3300, 1730, 1200 cm.$^{-1}$, $\delta$(CDCl$_3$) † 1.24, 1.40 (9H, broad singlets, 4'—CH$_3$ and

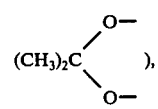

2.78 (3H, broad s, 3'—NCH$_3$), 7.22 and 7.27 ppm (15H, singlets, aromatic protons).

In general, the novel pseudotrisaccharides of this invention (I) can be used to treat diverse types of susceptible microbial, viral, helmintic and protozoal infestations. These anthelmintic, antiprotozoal, antimicrobial and antiviral activities can readily be determined by standard in vivo and in vitro tests well known to the microbiologist and virologist. Of the compounds of this invention it can generally be stated that those 6'—NH$_2$ or 6'—NHR$_4$ compounds having a 2'—OH group are preferred for their activity against bacteria, trichomonas, amoeba, and helminths; those 2'—HN$_2$ or 2'—NHR$_4$ compounds having a 6'—OH group are preferred for their activity against bacteria, trichomona, amoeba, and helminths; those 2'—$NH_2$ or 2'—$NHR_4$ compounds having a 6'—$NH_2$ or a 6'—$NHR_4$ group are preferred for their antibacterial activity while those 2'—OH or 6'—OH compounds are preferred for their antitrichomonal activity.

The preferred antibacterial compounds are gentamicin $X_2$, 3'-deoxygentamicin $X_2$, gentamicin B, 3'-deoxygentamicin B, JI-20A, 3'-deoxy JI-20A, 3'-deoxy-6'-N-methyl-gentamicin B, and 3'-deoxy-6'-N-methyl-JI-20A. The preferred antitrichomonal compounds are gentamicin $X_2$, 3'-deoxygentamicin $X_2$, gentamicin B, 3'-deoxygentamicin B, glucosyl garamine, 2'-N-ethyl gentamicin $X_2$, 2'-N-ethyl-3'-deoxygentamicin $X_2$. The preferred antiamoebal compounds are gentamicin $X_2$, 3'-deoxygentamicin $X_2$, gentamicin B, 3'-deoxygentamicin B, 2'-N-ethyl-gentamicin $X_2$, 2'-N-ethyl-3'-deoxygentamicin $X_2$. The preferred antihelmintics are gentamicin $X_2$, 3'-deoxygentamicin $X_2$, 2'-N-ethyl-gentamicin $X_2$, 2'-N-ethyl-3'-deoxygentamicin $X_2$, gentamicin B, 3'-deoxygentamicin B, and 6'-N-methyl 3'-deoxygentamicin B.

Typical activity is illustrated by the following tables showing antibacterial and antiprotozoal activities.

and other animal species. Furthermore, the compounds of this invention are capable of providing a method for preserving certain medical, veterinary and cosmetic preparations from microbial deterioration which comprises incorporating said compound in the preparation in which the preservation is desired.

When used topically or locally, the novel compounds (I) may be formulated into dosage forms wherein the compounds represent about 1 to about 10% by weight. In those instances when the dosage form is intended for oral administration, the compounds of this invention may be administered so as to provide from about 10 to about 100 mg. per kilogram of body weight per day. If the parenteral route is employed a dosage range of about 2 to about 10 mg. per kilogram of body weight per day is employed.

The compounds of this invention (I) may be formulated into dosage forms as the sole active ingredient or used in combination with other active ingredients.

The pharmaceutical formulations adapted for carrying the compound of this invention vary according to the mode and site of administration desired and the determination of the appropriate form is within the pharmaceutical arts. Exemplifying vehicles intended to Table I Minimal Inhibitory Concentration (MIC) (mcg/ml)

| Organism | Gentamicin $X_2$ | 2'-N-ethyl-Gentamicin $X_2$ | 3'-deoxy-Gentamicin $X_2$ | 3'-deoxy-2'-N-ethyl-Gentamicin $X_2$ | JI-20A | 3'-deoxy-JI-20A | 3'-deoxy-6'-N-methyl-Gentamicin B |
|---|---|---|---|---|---|---|---|
| *Staphylococcus aureus* | 0.3–7.5 | 3.0–7.5 | 0.5–7.5 | 7.5–>25 | 0.3 | 0.08–0.3 | <0.1–0.3 |
| *Streptococcus pyogenes* C | 1.0–17.5 | 3.0–>25 | 3.0–>25 | >25 | 17.5 | 0.8–7.5 | <0.1–17.5 |
| *Bacillus subtilis* | 0.08 | 3.0 | 0.03 | >25 | <0.05 | <0.05 | <0.1 |
| *Escherichia coli* | 0.8–3.0 | 3.0–>25 | 3.0–7.5 | 7.5–>25 | 0.3 | 0.08 | <0.1–0.75 |
| *Escherichia coli* (N,K resistant) | >25 | >25 | 3.0–7.5 | 17.5 | 17.5–>25 | 0.08–0.8 | 0.75–17.5 |
| *Escherichia coli* (G resistant) | >25 | 17.5–>25 | >25 | >25 | >25 | >25 | 7.5–>25 |
| *Escherichia coli* (T resistant) | >25 | >25 | 17.5 | 3.0 | >25 | 17.5 | >25 |
| *Pseudomonas aeruginosa* | 3.0–>25 | 17.5–>25 | 3.0–7.5 | 3.0–>25 | 7.5–17.5 | 0.08–0.8 | <0.1–3.0 |
| *Pseudomonas aeruginosa* (G resistant) | >25 | >25 | >25 | >25 | >25 | >25 | 3.0–>25 |
| *Klebsiella pneumoniae* (N,M resistant) | >25 | >25 | 0.8–3.0 | 3.0–7.5 | >25 | 0.08 | 0.3–0.75 |
| *Klebsiella pneumoniae* (G-resistant) | >25 | >25 | >25 | >25 | >25 | 7.5–>25 | >25 |
| *Providence* | >25 | >25 | >25 | >25 | >25 | >25 | 3.0 |
| *Proteus mirabilis* | 3.0 | >25 | 7.5 | >25 | 7.5 | 0.3 | 0.75–3.0 |
| *Salmonella typhimurium* | | 3.0 | 7.5 | | 0.3 | 0.75 | |
| *Serratia marcessans* | >25 | >25 | 0.8 | 3.0 | >25 | 3.0 | 3.0 |

In Table I:
N = neomycin
K = kanamycin
G = garamycin
T = tobramycin

Table II

In vitro Activity Against *Trichomonas Vaginalis*

| Compound | Minimal 99% suppression level (mcg/ml) | | Minimal Cidal Level (mcg/ml) | |
|---|---|---|---|---|
| | 24 hr. | 48 hr. | 24 hr. | 48 hr. |
| Gentamicin $X_2$ | 10 | <10 | 10 | 10 |
| 2'-N-Ethylgentamicin $X_2$ | <10 | <2.5 | 10 | 2.5 |
| 3'-Deoxygentamicin $X_2$ | 10 | <10 | 10 | 10 |
| 3'-Deoxy-2'-N-ethylgentamicin $X_2$ | <2.5 | <2.5 | <2.5 | <2.5 |
| O-α-D-Glucopyranosyl-(1 4)-garamine | 10 | <10 | 25 | 10 |

STS - Simplified Tripticase Serum Medium, Baltimore Biological Laboratories, Baltimore, Maryland.

The novel compounds of this invention (I) are useful in their pharmacological application for treating conditions caused by susceptible organisms in both humans carry this product for topical application are creams, lotions, solutions, ointments, dusting powders, gels suspensions, and aerosols having propellants such as chlorofluoralkane mixtures, Freon 11 and Freon 12 mixture.

Other suitable dosage forms include vaginal suppositories, tablets, capsules, ophthalmic, otic and nasel solutions, shampoos and injectables. The compound of this invention may also be administered to animals by admixing it with their feed.

The following formulations are representative of pharmaceutical compositions containing compounds of this invention.

| Formulation 1 | | |
|---|---|---|
| PARENTERAL SOLUTION | mg/ml | mg/10 ml |
| 3'-Deoxygentamicin $X_2$ | 40 to 200 mg. | 400 – 2000 mg. |
| Methylparaben | 1.8 mg. | 18 mg. |

-continued

| Formulation 1 | | |
|---|---|---|
| PARENTERAL SOLUTION | mg/ml | mg/10 ml |
| Propylparaben | 0.2 mg. | 2 mg. |
| Water for injection q. s. | 1.0 ml. | 10.0 ml. |

Place 70% of the water for injection into a suitable mixing vessel and heat to 70° C. Add the methylparaben and proplyparaben and mix until dissolved. Cool the above solution to 25° –30° C. Pass a stream of nitrogen gas through the solution. Add the 3'-deoxygentamicin $X_2$ and mix until dissolved. Bring the solution to final volume. Pass the solution through a suitable sterilizing filter, employing appropriate aseptic techniques. Fill the solution into suitable sterile containers employing appropriate aseptic filling techniques.

| Formulation 2 | |
|---|---|
| ORAL SYRUP | PER LITER |
| 3'-Deoxy JI-20A | 100 g. |
| Standard Granulated Sugar | 550 g. |
| Sorbitol Solution | 200 g. |
| Preservatives, Sufficient | — |
| Purified Water, to make | 1.0 liter |

Add the 3'-deoxy JI-20A, standard granulated sugar, sorbitol solution, preservatives to approximately 350 ml. of purified water contained in a suitable mixing vessel. Mix until a solution is obtained. Add sufficient purified water to make 1 liter. Pass solution through a suitable clarifying filter.

| Formulation 3 | |
|---|---|
| TOPICAL CREAM | PER KG. |
| 3'-Deoxygentamicin $X_2$ | 10 g. - 100 g. |
| Ethoxylated Cetyl/Stearyl Alcohol | 20 g. |
| Cetyl Alcohol | 35 g. |
| Stearyl Alcohol | 35 g. |
| Petrolatum | 200 g. |
| Mineral Oil | 50 g. |
| Buffers, Sufficient | — |
| Preservatives, Sufficient | — |
| Purified water to make | 1.0 kg. |

Add the cetyl alcohol, stearyl alcohol, ethoxylated acetyl/stearyl alcohol, petrolatum and mineral oil to a suitable mixing vessel. Heat to 80° C to melt. Mix. Add the preservatives, buffers and 3'-deoxygentamicin $X_2$ in approximately 95% of the purified water heated to 80° C in a suitable mixing vessel. Mix. Add the melted wax phase to the aqueous phase and mix while cooling to approximately 40° C. Add sufficient purified water to make 1 kg. Mix until cool.

| Formulation 4 | |
|---|---|
| TOPICAL OINTMENT | PER KG. |
| 3'-Deoxygentamicin $X_2$ | 10 g. - 100 g. |
| White Petrolatum, to make | 1.0 kg. |

Melt and heat the petrolatum to 50° C in a suitable mixing vessel. Remove a portion of the melted petrolatum and make a slurry of the 3'-deoxygentamicin $X_2$. Pass the slurry through a suitable colloid mill and mill until a uniform dispersion is obtained. Add the milled slurry to the remainder of the melted petrolatum and mix until cool.

| Formulation 5 | |
|---|---|
| TABLETS | PER TABLET |
| 3'-Deoxygentamicin $X_2$ | 25.0 mg. |
| Lactose, Impalpable Powder | 190.0 mg. |
| Corn Starch | 25.0 mg. |
| Polyvinylpyrrolidone | 7.5 mg. |
| Magnesium Stearate | 2.5 mg. |
| Alcohol, SD 3A q.s. | |

Place the 3'-deoxygentamicin $X_2$, lactose and the corn starch into a suitable mixing bowl and mix. Prepare a solution of the polyvinylpyrrolidone in alcohol. Use this solution to prepare a damp mass of the powders. Screen the damp mass to produce granules. Dry the granules. Reduce the dried granules to a specific particle size. Add the magnesium stearate (lubricant) mix and compress the granulation into tablets using suitable tableting equipment.

| Formulation 6 | |
|---|---|
| HARD GELATIN CAPSULES | PER CAPSULE |
| 3'-Deoxygentamicin $X_2$ | 25.0 mg. |
| Lactose, Impalpable Powder | 224.0 mg. |
| Magnesium Stearate | 1.0 mg. |

Place the 3'-deoxygentamicin $X_2$ and lactose into a suitable mixing bowl and mix. Pass the mixed powders through a mill. Add the mixed milled powders to a suitable mixing vessel and mix again. Pre-mix the magnesium stearate with a portion of the batch from above. Pass the pre-mixed magnesium stearate of the batch and mix. Fill into empty gelatin capsules using suitable encapsulating equipment.

I claim:

1. A compound represented by the structural formula:

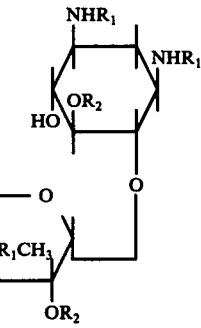

wherein $R_1$ is an amino protective group or hydrogen and $R_2$ is an hydroxy protective group or hydrogen.

2. A compound according to claim 1 wherein $R_1$ and $R_2$ are hydrogen, said compound being garamine.

3. A compound according to claim 1 wherein $R_1$ is an amino protective group and $R_2$ is hydrogen.

4. A compound according to claim 3 wherein said amino protective group is carbobenzoxy, t-butoxycarbonyl, dinitrophenyl, 2,2,2-trichloroethoxycarbonyl, ethoxycarbonyl, methoxycarbonyl, acetyl, benzoyl, 2-iodoethoxycarbonyl, or p-methoxycarbobenzoxy.

5. A compound according to claim 4 wherein $R_1$ is carbobenzoxy.

6. A compound according to claim 1 wherein $R_1$ is an amino protective group and $R_2$ is an hydroxy protective group.

7. A compound according to claim 6 wherein $R_2$ is acetyl, 2,2,2-trichloroethylcarbonyl, benzyl or p-nitrobenzyl.

8. A compound according to claim 7 wherein $R_2$ is acetyl.

9. A compound according to claim 7 wherein $R_1$ is carbobenzoxy, t-butoxycarbonyl, dinitrophenyl, 2,2,2-trichloroethoxycarbonyl, ethoxycarbonyl, methoxycarbonyl, acetyl, benzoyl, 2-iodoethoxycarbonyl, or p-methoxycarbobenzoxy.

10. A compound according to claim 9 wherein $R_1$ is carbobenzoxy and $R_2$ is acetyl.

11. Compound of the general formula:

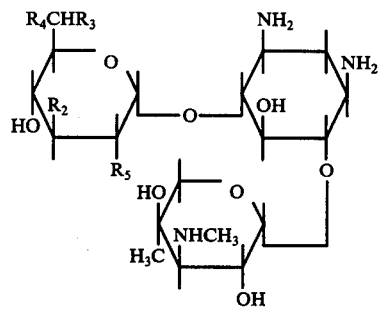

and their pharmaceutically acceptable acid addition salts and Schiffs-base oxazolidine derivatives, wherein $R_2$ is hydrogen or hydroxy, $R_3$ and $R_5$ are each hydroxy, or $NHR_4$, $R_4$ is hydrogen or lower alkyl with the provisos (a) that when $R_2$ is hydroxy, $R_4$ is H or $CH_3$ and $R_3$ is OH or $NH_2$, then $R_5$ is other than $NH_2$ (b) that when both $R_2$ and $R_5$ are hydroxy, and $R_4$ is H or $CH_3$ then $R_3$ is other than $NH_2$.

12. A compound of claim 11 wherein $R_2$ and $R_3$ are hydroxy and $R_5$ is other than hydroxy.

13. A compound of claim 11, wherein $R_2$ and $R_4$ are hydrogen, $R_3$ is OH and $R_5$ is $NH_2$.

14. A compound of claim 11 wherein $R_2$ and $R_4$ are hydrogen, $R_3$ is OH and $R_5$ is NH ethyl.

15. A compound of claim 11 wherein $R_2$ and $R_4$ are hydrogen, $R_3$ is $NH_2$ and $R_5$ is OH.

16. A compound of claim 11 wherein $R_2$ and $R_4$ are H, $R_3$ is $NHCH_3$ and $R_5$ is OH.

17. A compound of claim 11, wherein $R_2$ and $R_4$ are H, and $R_3$ and $R_5$ are $NH_2$.

18. A compound of claim 11 wherein $R_2$ and $R_4$ are H, $R_3$ is $-NHCH_3$ and $R_5$ is $NH_2$.

* * * * *